United States Patent [19]

Saito et al.

[11] Patent Number: 4,790,664
[45] Date of Patent: Dec. 13, 1988

[54] DEVICE AND METHOD FOR MEASURING OPTICAL PROPERTIES

[75] Inventors: Kenji Saito, Tokyo; Ken Eguchi, Atsugi; Haruki Kawada, Atsugi; Yoshinori Tomida, Atsugi; Takashi Nakagiri, Tokyo; Yukuo Nishimura, Sagamihara; Kiyoshi Takimoto, Atsugi, all of Japan

[73] Assignee: Canon Kabushiki Kaisha, Tokyo, Japan

[21] Appl. No.: 897,055

[22] Filed: Aug. 15, 1986

[30] Foreign Application Priority Data

| Aug. 16, 1985 | [JP] | Japan | 60-179398 |
| Aug. 16, 1985 | [JP] | Japan | 60-179399 |
| Aug. 16, 1985 | [JP] | Japan | 60-179400 |
| Dec. 16, 1985 | [JP] | Japan | 60-281107 |
| Dec. 16, 1985 | [JP] | Japan | 60-281108 |
| Dec. 16, 1985 | [JP] | Japan | 60-281109 |
| Dec. 16, 1985 | [JP] | Japan | 60-281110 |

[51] Int. Cl.⁴ .................................. G01N 21/00
[52] U.S. Cl. .................................. 356/432; 356/128
[58] Field of Search ............... 356/432 T, 432 R, 128; 374/5, 57, 121

[56] References Cited

U.S. PATENT DOCUMENTS

| 3,472,598 | 10/1969 | Hossmann | 356/128 |
| 4,243,327 | 1/1981 | Moacanin et al. | 356/432 T |
| 4,299,494 | 11/1987 | Badoz et al. | 356/128 |
| 4,468,136 | 8/1984 | Murphy et al. | 356/128 |
| 4,522,510 | 6/1985 | Rosencwaig et al. | 356/432 T |
| 4,529,319 | 7/1985 | Muller | 356/432 T |
| 4,579,463 | 4/1986 | Rosencwaig et al. | 356/432 T |
| 4,634,290 | 1/1987 | Rosencwaig et al. | 356/432 T |
| 4,666,308 | 5/1987 | Williams | 356/432 T |

Primary Examiner—Bruce C. Anderson
Attorney, Agent, or Firm—Fitzpatrick, Cella, Harper & Scinto

[57] ABSTRACT

A device for measuring optical properties is provided which is equipped with an exciting light source for emitting exciting light to the sites to be measured of a sample, a light intensity modulator for modulating the exciting light, a probe light source for emitting probe light and a detector for receiving the probe light. The device is characterized by comprising an intensity distribution modifying means for bringing the maximum intensity portion of said probe light close to the sample when the probe light emitted from the probe light source reaches the site to be measured or the vicinity thereof. A method for measuring optical properties using the device is also provided. This device is useful particularly for measurement of the light absorption characteristics of a monomolecular film spread on a liquid surface.

10 Claims, 22 Drawing Sheets

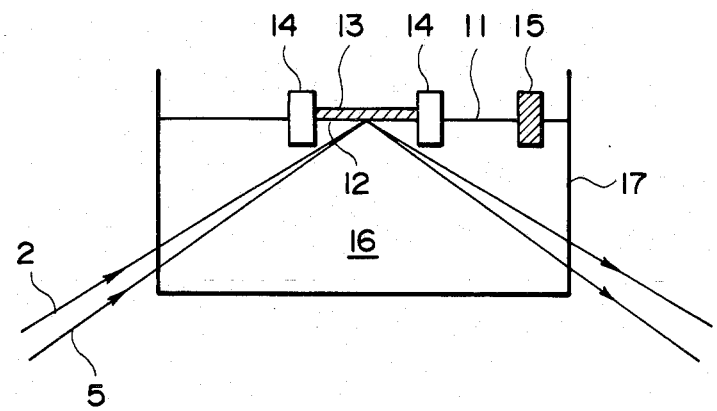
F I G. 6A
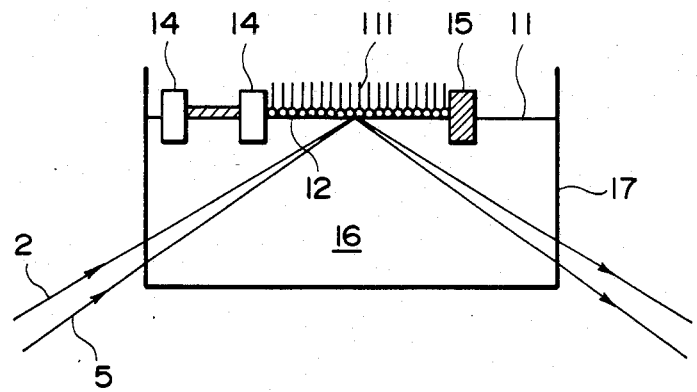
F I G. 6B

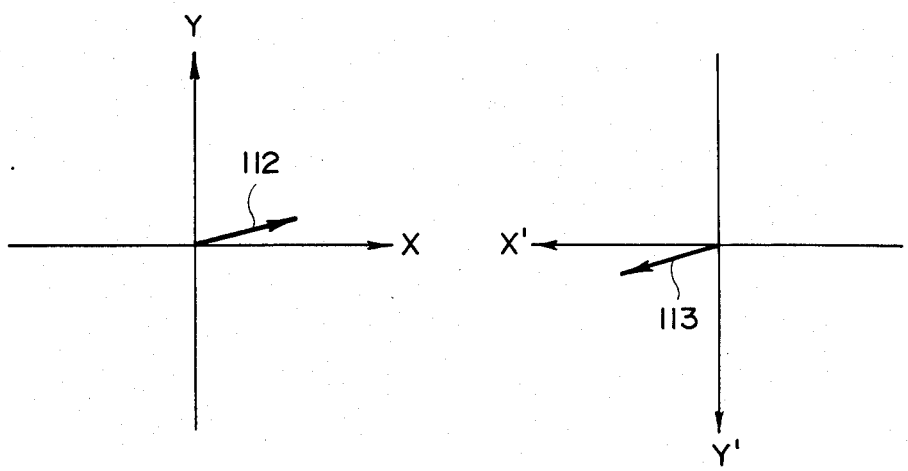
F I G. 11A    F I G. 11B
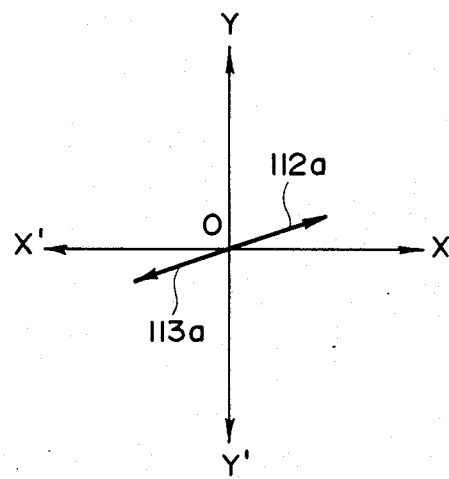
F I G. 11C

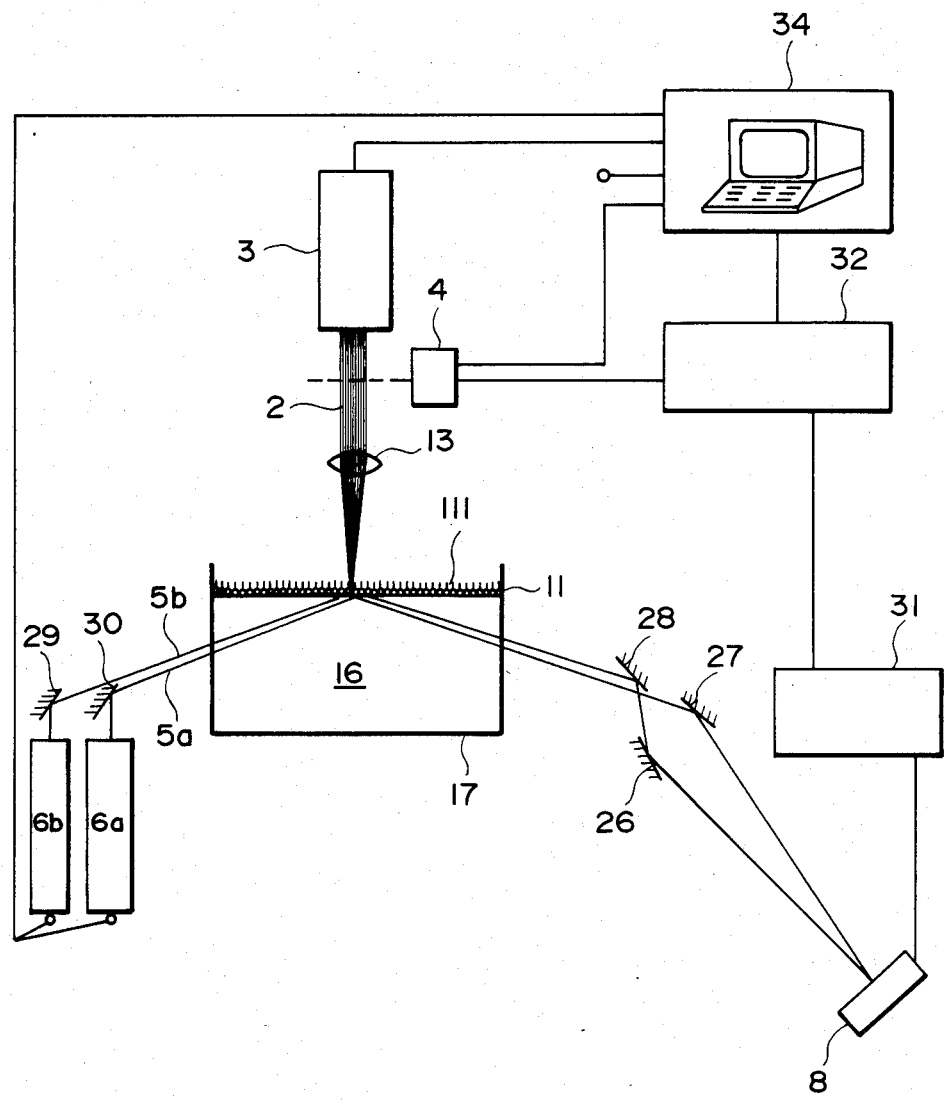
F I G. 14

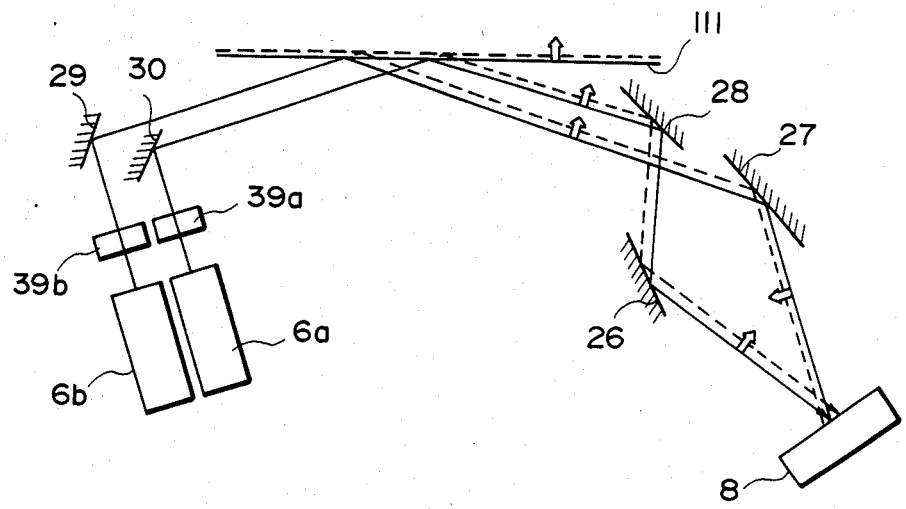
F I G. 17
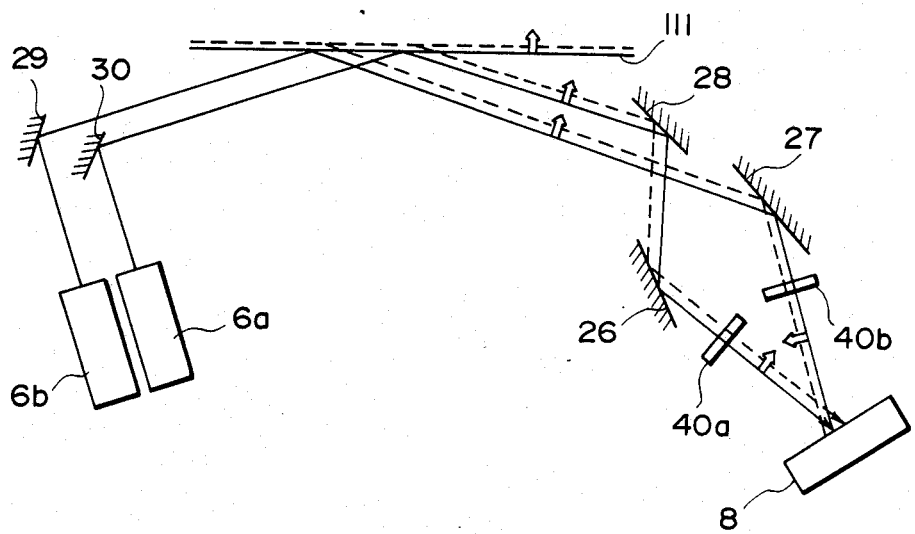
F I G. 18

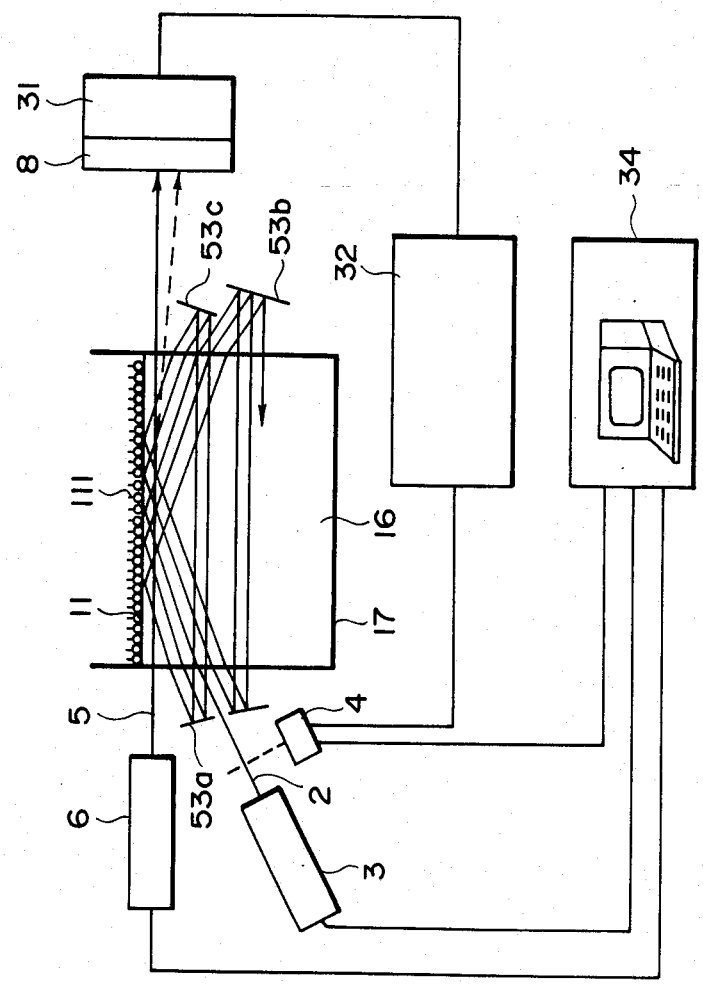
F I G. 21

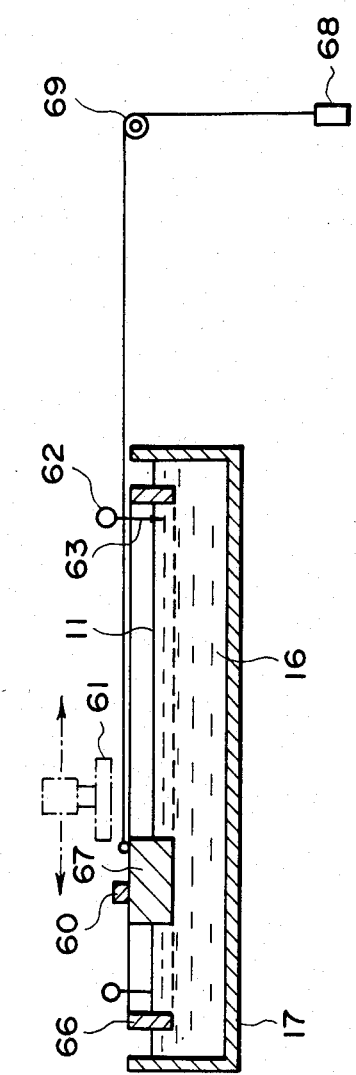
F I G. 36

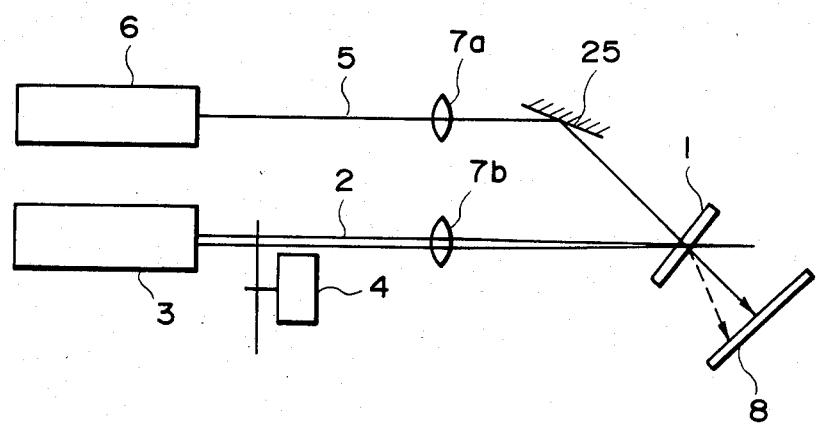
F I G. 37A
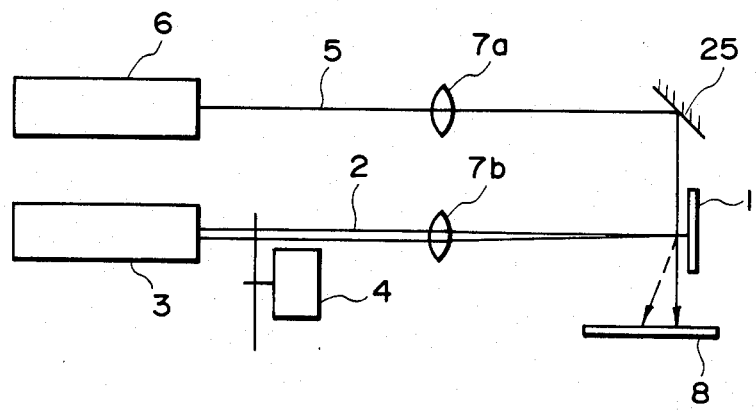
F I G. 37B

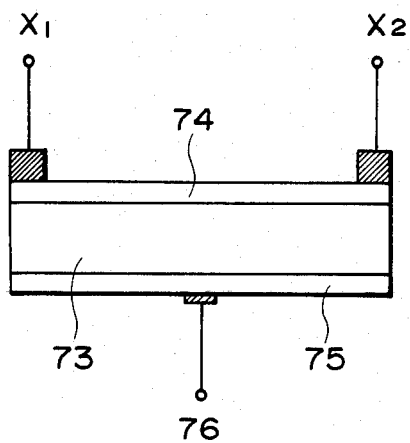
F I G. 38
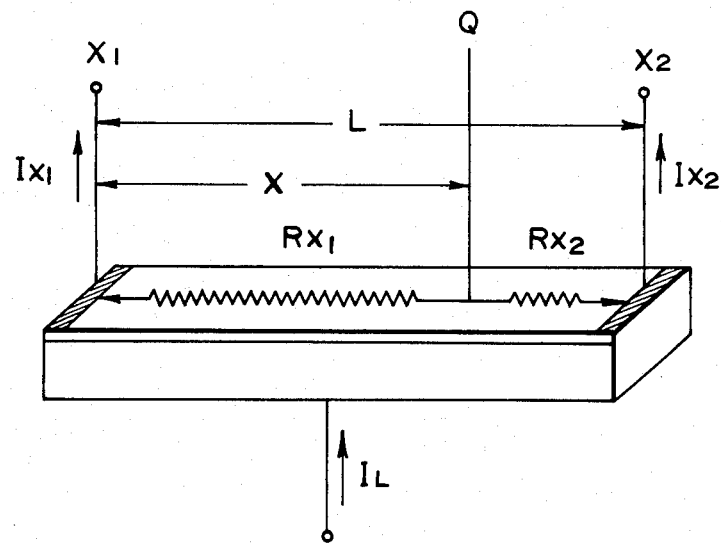
F I G. 39

DEVICE AND METHOD FOR MEASURING OPTICAL PROPERTIES

BACKGROUND OF THE INVENTION

1. Field of the Invention

This invention relates generally to a device and a method for measuring optically the physical properties of solids, liquids and gases, and more particularly to a device and a method for measuring optically the characteristics of a thin film spread on a liquid surface. The present invention is utilized for measurement of the light absorption characteristics which are the basis for various characteristics analysis of thin films, for example, for characteristic analysis of a monomolecular film spread on a liquid surface to be built up during formation of a monomolecular built-up film.

2. Related Background Art

As a device for measuring light absorption characteristics of a material, there is a device for determining light absorption characteristics from transmittance and reflectance. However, when light is irradiated on a material to be measured, light scattering occurs in addition to transmission and reflection of light, and thus direct measurement of the absorbed light component is important in evaluation of light absorption characteristics to achieve a higher precision of measurement.

As a device for measuring directly the light absorbing components, there is Photoacousatic Spectroscopy (PAS) or Photothermal Radiometry (PTR), which is a measuring device utilizing intermittent conversion of light energy to thermal energy according to a radiationless relaxation process of the light energy absorbed by the material to be measured when light is intermittently irradiated thereon.

There is also a device called Photothermal Deflection Spectroscopy (PDS) for measuring directly the light absorbing components. This PDS device works based on the phenomenon that refractive index changes by temperature distribution caused within the material to be measured or in the vicinity thereof by heat generated by light absorption in the material, whereby the light introduced thereto is deflected. That is, on the measuring site of a material, exciting light which changes the refractive index by creating a temperature distribution by heat generation when the light is absorbed and a probe light for measuring the degree of deflection in terms of the change in a refractive index are irradiated, and the light absorption characteristics of the material to be measured are measured from the wavelength of the exciting light and the deflection of the probe light. The device allows to provide a material to be measured and a detecting system independently of each other and is suitable for measurement at the site where the material is prepared and for remote measurement apart from the site. The basic principle of the present invention is common to this PDS device.

The above-mentioned PDS device is inclusive of the two types of the transverse type and the collinear type according to arrangement of the exciting light and the probe light. Both of the types measure the deflection degree of the probe light corresponding to the amount of exciting light absorbed by the material to be measured as mentioned above, and a position sensitive detector (PSD) is frequently used as the detector.

FIG. 37A shows an example of the collinear type, in which the exciting light 2 emitting from the exciting light source 3 is made intermittent or accentuated with the light intensity modulator 4, condensed at the lens 7b to irradiate the material to be measured 1. The probe light 5 emitting from the probe light source 6 transmits through the measuring site of the material 1 on which the exciting light 2 is irradiated by means of an optical path controller such as the lens 7a or a mirror, etc. to reach the detector 8, where the deflection degree when deflected as shown by the dotted line is measured. FIG. 37B is an example of the transverse type, and the probe light 5 is irradiated in parallel to the surface of the material to be measured 1, as different from the collinear type, otherwise being the same as the collinear type.

The PDS device can be theoretically dealt with by solving the thermal conduction equation within the material to be measured. The deflection degree measured in terms of the deflection angle $\phi$ is proportional to the exciting light intensity, the temperature coefficient of the refractive index $(\partial n/\partial n)$, and the temperature gradient $(\partial T/\partial x)$ in the region where the probe light passes, etc. The item proportional to the light absorption coefficient of the material to be measured is included in $(\partial T/\partial x)$. Also, the $(\partial n/\partial T)$ can take either a positive or negative value depending on the material to be measured and this means that the deflection angle can be either positive or negative.

FIG. 38 is a longitudinal sectional view showing a construction example of one-dimensional PSD. In FIG. 38, the one-dimensional PSD constitutes a uniform resistance layer 74 of P layer on the surface of a flat plate silicon 73, and has electrodes $X_1$ and $X_2$ provided on both sides thereof, having also a common electrode 76 at the N layer 75 on the back.

FIG. 39 is a schematic illustration showing its actuation principle. The light-forming electric charges made correspondent to the incident position of the light Q reaches the above resistance layer 74 as the photocurrent corresponding to its energy to be divided in inverse proportion to the distances from its position Q to the take-out electrodes $X_1$ and $X_2$ at the both ends and outputted from the respective electrodes. If the photocurrent is defined as $I_L$, the photocurrent $I_{x1}$ and $I_{x2}$ outputted from the electrodes $X_1$ and $X_2$ are represented as follows:

$$I_{x1} = I_L \cdot R_{x2}/(R_{x1} + R_{x2})$$

$$I_{x2} = I_L \cdot R_{x1}/(R_{x1} = R_{x2})$$

and further, since the resistance between $X_1$ and $X_2$ is maintained at uniform distribution, the following respective equations are valid between the resistance between $X_1$ and $X_2$ and the length L:

$$R_{x1} + R_{x2} = L$$

$$R_{x1} = X$$

$$R_{x2} = L - X$$

Accordingly, the signals taken out from the respective electrodes can be represented by L and x as follows:

$$I_{x1} = I_L \cdot (L - X)/L$$

$$I_{x2} = I_L \cdot X/L$$

Thus, the informations of the incident position of light and light intensity can be obtained at the electrodes of $X_1$ and $X_2$.

Further, by taking a ratio of the difference between $I_{x1}$ and $I_{x2}$ to the sum thereof and representing it as P, the following equation can be obtained:

$$P = \frac{I_{x1} - I_{x2}}{I_{x1} + I_{x2}} = \frac{L - 2x}{L}$$

and the positional signals irrelevant with light intensity change can be obtained continuously corresponding to $x=0$ to L as follows:

$$x = 0, P = 1$$
$$x = \tfrac{1}{2}, P = 0$$
$$x = L, P = -1$$

Having described about the one-dimensional case, the two-dimensional case may also be considered similarly, and the positional signals can be determined from the block diagram of the actuation circuit as shown in FIG. 40.

Here, from the actuation principle of PSD, when light is introduced at two or more points, the positional signal weighted in proportion to the respective light intensity is obtained. Also, in the case when the light flux is expanded, the positional signal corresponding to the gravitational center of light intensity can be obtained.

On the other hand, there has been known in the art a device for forming monomolecular built-up films in which monomelecular films are transferred onto a substrate by laminating them one by one according to the monomolecular layer film built-up method called the Langmuir-Blodgett method (hereinafter called LB method) named after the inventors (see Shin Jikken Kagaku Koza (New Course of Experimental Chemistry), Vol. 18, pp. 498–507, Maruzen).

The above device is constituted schematically by a liquid tank containing a liquid, a film-forming frame which is floated so as to divide the liquid surface into two and is capable of two-dimensional piston movement, a driving means for moving the film-forming frame, a surface-pressure-measuring instrument for measuring the surface pressure of the monomolecular film spread on the liquid surface and a substrate holder for moving the substrate held vertically relative to the liquid surface. Formation of a monomolecular film and transfer thereof onto a substrate are practiced as described below.

First, with the film-forming frame being kept at one side of the liquid tank, a solution of a film-forming substance dissolved into a volatile solvent such as benzene, chloroform, etc. at a concentration of, for example, ca. $5 \times 10^{-3}$ mol/liter is added in several drops onto the liquid surface by means of a fountain pen filler, etc. When the solution is spread over the liquid surface and the solvent is evaporated, the monomolecular film remains on the liquid surface.

The above monomolecular film exhibits the behaviour of a two-dimensional system on the liquid surface. When the surface density of molecular is small, it is called as a gas film of two-dimensional gas, and the state equation of two-dimensional ideal gas is valid between the occupied area per molecule and the surface pressure.

Subsequently, by increasing the surface molecular density by narrowing the region of the liquid surface carrying the spread molecular film by moving gradually the film-forming frame, the interaction between molecules is intensified, whereby the gas film changes via a liquid film of two-dimensional liquid to a solid film of two-dimensional solid. When such a solid film is formed, the molecules become oriented fairly regularly and the film has highly ordered characteristic and uniform ultra-thin film characteristic. And, by moving vertically the substrate with the substrate holder, the monomolecular film which has become said solid film can be attached and transferred thereon. Also, by transferring the monomolecular film for plural times on the same substrate, a built-up monomolecular film can be obtained. As the substrate, there may be employed, for example, a glass, a synthetic resin, a ceramic, a metal, etc.

In order to practice the transfer operation under the preferable state of the monomolecular film for transfer onto the above substrate, the surface pressure of the monomolecular film is measured. The surface pressure preferable for transfer is generally accepted to be 15 to 30 dyn/cm. Outside this range, the alignment or orientation of the molecules may be disturbed, or otherwise peel-off of the film will readily occur. However, in a special case, for example, depending of the chemical structure of the film-forming substance, the temperature conditions, etc., preferable values of the surface pressure may be outside the above range, and therefore the above range may be a tentative measure.

The surface pressure of the above monomolecular film is measured automatically and continuously by means of a surface-pressure-measuring instrument. As the surface-pressure-measuring instrument, there is one in which the method for determining the difference in surface tension between the liquid surface covered with no monomolecular film and the liquid surface covered with monomolecular film is applied, or one in which the two-dimensional pressure applied on the film-forming frame which will float by partitioning the liquid surface into the liquid surface covered with no monomolecular film and the liquid surface covered with monomolecular film, etc., each having specific features. The occupied area per molecule constituting monomolecular film and the degree of the change are also generally measured together with the surface pressure. The occupied area and its change can be determined from the movement of the film-forming frame.

The movement is controlled based on the surface pressure of the monomolecular film measured by means of the above measuring instrument. More specifically, the driving means for moving the film-forming frame is controlled based on the surface pressure of monomolecular film measured by the surface pressure measuring instrument so that the monomolecular film can constantly maintain a predetermined surface pressure selected within the preferable range for transfer operation. The movement control of the film-forming frame is continuously made not only until initiation of the transfer operation of monomolecular film after dropwise addition of the film-forming substance, but also during the transfer operation continuously. For example, in the transfer operation, as the monomolecular film is transferred onto the substrate, the surface density of the monomolecular-film-forming molecules on the liquid surface will be lowered, whereby the surface density will be also lowered. Accordingly, by moving the film-forming frame, the spreading area of the monomolecular film is narrowed thereby to maintain the constant surface pressure by correction corresponding to the lowered surface pressure.

However, when a PAS device, PTR device or PDS device itself is to be used for measurement of an extremely thin material under a specific environment such as a thin film of monomolecular film being spread on liquid surface, problems arise such as difficulty of measurement, liability of declining precision, sensitivity of measurement because of the location on a liquid surface of the extreme thinness of the measured material.

PAS devices can be classified into the microphone system and the piezoelectric element system depending on the kind of the detector. In the case of the microphone system, a sample is required to be placed in a hermetically sealed sample chamber, while in the case of the piezoelectric element system, arrangement of the detector and the sample is restricted. Thus, either one of them is not suitable for measuring a thin film as spread on a liquid surface.

In the case of the collinear type PDS device, since the probe light passes through the measuring site of the thin film where the greatest refractive index change occurs by irradiation of exciting light, there is the advantage that a relatively greater positional change of probe light can be obtained on the detector. However, in the collinear type PDS device, since the probe light transmits through the thin film which the material to be measured, it receives at the same time the influences from both the liquid phase and the gas phase of which refractive index varies based on exciting light absorption of the thin film. Accordingly, no correct measurement is possible unless the variation in refractive index between the liquid phase and the gas phase is considered, whereby there is the problem that measurement of high precision becomes extremely difficult.

Also, when the material to be measured is a thin film as in the present invention, the refractive index change of the surrounding caused by absorption of exciting light is small. Accordingly, in the case of a transfer type PDS device, it is required that the probe light be brought close to the thin film on the liquid surface so that it can pass through the region where refractive index change as great as possible occurs. Particularly, since the detector of the PDS device has the property of detecting the position of the "gravitational center" of the light-receiving intensity, and it is preferred that the flux center of the probe light with strong light intensity be nearer to the thin film. However, it is not possible to access the center of the probe flux nearer than its radius. Therefore the probe flux center with strong light intensity is liable to pass through the region apart from the thin film, resulting in little refractive index change. This makes a high precision and high sensitivity measurement difficult.

In PDS measurement, the convergence state of the fluxes of exciting light and probe light have influences on sensitivity, and the relative positional relationship between exciting light and probe light will affect sensitivity greatly. Accordingly, it is necessary to monitor the irradiation positions of exciting light and probe light and their relative positions and, in prior art, scattered light from excitation light and probe light have been monitored by visual observation with a microscope, but such a method will give undesired external disturbance such as vibration of liquid surface. Also, in the case of a very thin or homogeneous film, the scattered light may be sometimes undetectable. Further, in carrying out measurement of light absorption characteristics, the wavelength of the light used is not limited to a visible light region and, for example, in the case of using IR-ray, there has been the drawback that the irradiation position cannot be confirmed by visual observation.

Further, concerning measurement of a material spread on the liquid surface such as monomolecular film, noise by wobbling of the liquid surface brings about lowering in measurement precision.

On the other hand, as described above, various fine controls are required for obtaining a monomolecular built-up film. However, many experiments must be conducted in order to search the optimum condition, and it can be confirmed only indirectly by the surface pressure, etc. whether the monomolecular film on the liquid surface is in the suitable condition for built-up or not, and thus precision is insufficient. This can be improved by grasping directly the physical properties of the monomolecular film on the liquid surface by means of PAS, PTR or PDS device, but due to the problems as mentioned above, such a demand cannot be met under the present situation.

SUMMARY OF THE INVENTION

An object of the present invention is to provide a device and a method for measuring light absorption characteristics of a sample which is very thin and under a specific environment of a thin film being spread on liquid surface with high precision and sensitivity.

The above object of the present invention can be accomplished as specified below.

That is, in accordance with the present invention, there is provided a device for measuring optical properties equipped with an exciting light source for emitting exciting light to the site to be measured of a sample, a light intensity modulator for modulating the exciting light, a probe light source for emitting probe light and a detector for receiving the probe light, comprising an intensity distribution modifying means for bringing the maximum intensity portion of said probe light close to the sample when the probe light emitted from the probe light source reaches the site to be measured or the vicinity thereof.

The present invention also provides a method for measuring optical properties by irradiating exciting light to the site to be measured of a sample and permitting the probe light irradiated on said site to be measured or the vicinity thereof to enter a detector and measuring the optical properties of said sample from the degree of deflection of the probe light, which comprises forming the flux of the probe light to an intensity distribution such that the maximum intensity at the site to be measured of the sample or the vicinity thereof may be closest to the sample.

Further, there is also provided a device for measuring optical properties, comprising a liquid tank for containing a liquid for spreading a thin film on a liquid surface, an exciting light source for emitting exciting light to be irradiated on the site to be measured of the thin film on the liquid surface, an optical intensity modulator for modulating intensity of the exciting light before reaching said measuring site, a probe light source for emitting probe light to irradiate said measuring site at an incident angle so as to be totally reflected against said liquid surface, a detector for detecting the degree of deflection of the probe light passed through said measuring site and an optical system interposed in the optical path of the proble light for stabilizing its deflected amount against fluctuations of the thin film.

Still further, the present invention provides a method for measuring optical properties by irradiating excited light onto the site to be measured of a sample and permitting a probe light irradiated on said site to be measured, or the vicinity thereof, to enter a detector. The optical properties of said sample are measured from the degree of deflection of the probe light, which comprises using two or more beams of the probe light and setting an optical system which makes the vector sum of the fluctuation from the standard point on the detecting surface of the respective beam of probe light caused by fluctuations of the sample invariably zero.

The above object of the present invention can also be accomplished by a device for measuring optical properties, comprising a liquid tank for containing a liquid for spreading a thin film on a liquid surface, an exciting light source for emitting exciting light to irradiate the site to be measured of a thin film on the liquid surface at an incident angle so as to be totally reflected at said liquid surface, and an optical system for permitting the exciting light totally reflected at the above liquid surface to be incident again onto the site to be measured at an angle so as to be totally reflected against the liquid surface. The device further comprises an optical intensity modulator for modulating the intensity of the exciting light before reaching the site to be measured, a probe light source for emitting the probe light passing through the site to be measured or the vicinity thereof, and a detector for detecting the degree of the deflection of the probe light passed through the site to be measured or the vicinity thereof.

BRIEF DESCRIPTION OF THE DRAWINGS

FIGS. 6A, 6B, 7, 8, and 9 show an example of the present invention for measurement of light absorption characteristics of a monomolecular film spread on a liquid surface.

FIGS. 11A, 11B, and 11C show coordinate diagrams illustrating the basic principle of the compensation of fluctuation present invention.

FIG. 14 is a constitutional illustration showing one example of a device for forming a monomolecular built-up film in practicing the present invention.

FIGS. 17 through 20 are schematic constitutional illustrations showing embodiments of the present invention provided with control means for making doses of the two probe lights equal on the light receiving surface of the detector.

FIG. 21 is a schematic illustration of a device for measuring light absorption characteristics of a thin film of the present invention.

FIGS. 35 and 36 illustrate an apparatus for obtaining a monomolecular built-up film.

FIG. 37A shows an example of a collinear type of arrangement of exciting light and probe light.

FIG. 37B shows an example of a transverse type of arrangement of exciting light and probe light.

FIG. 38 is a longitudinal sectional view showing a construction example of one-dimensional PSD.

FIG. 39 is a schematic illustration showing the actuation principle of the present invention.

DETAILED DESCRIPTION OF THE PREFERRED EMBODIMENTS

When exciting light is absorbed by the thin film to be examined, the refractive index at the measuring site and the vicinity thereof changes on irradiation of the exciting light from that on non-irradiation, and therefore light absorption characteristics can be measured by detecting this change as the degree of deflection of the probe light. This principle itself is the same as the PDS method of the prior art.

In the present invention, in the first place, from the observation that the light position detector will finally output a positional signal as to the gravitational center of the light intensity distribution, a modifying means for intensity distribution of light flux is provided so that the maximum intensity portion of the probe light may pass through the refractive index fluctuation region with the greatest deflection.

Referring now to preferred embodiments and the drawings thereof, detailed description is given.

Figure 1:
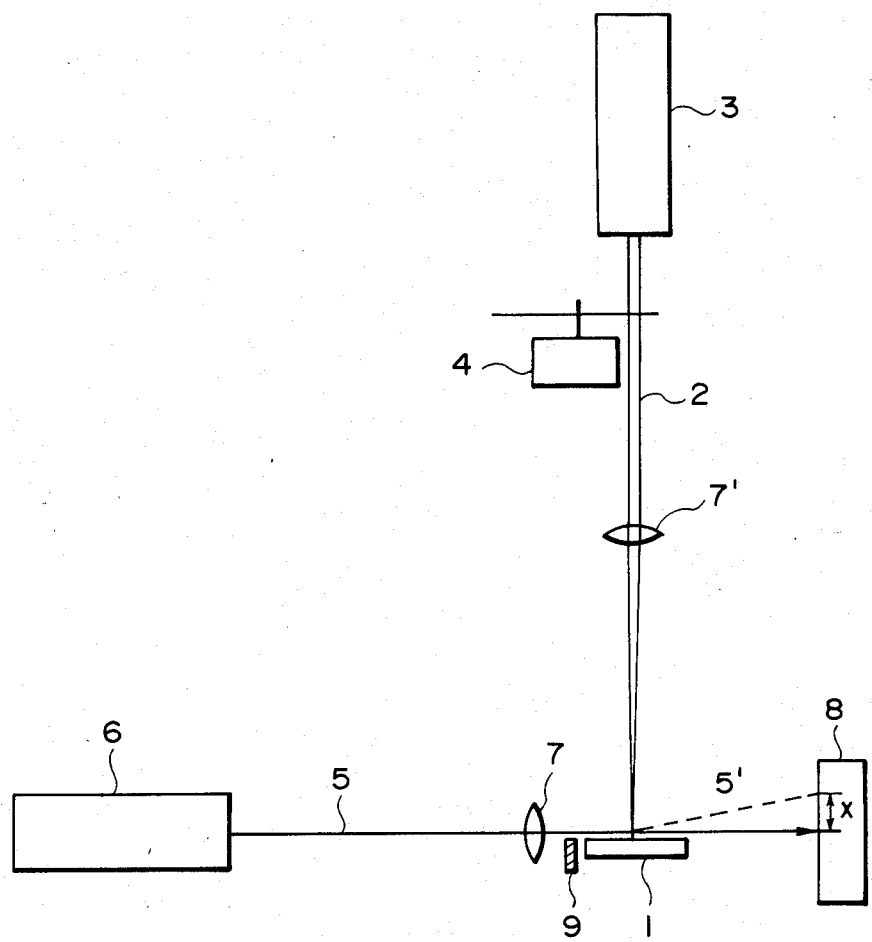
FIG. 1 is a schematic constitutional view showing an example of the device for measuring optical properties for practicing the present invention.

FIG. 1 is a schematic constitutional view showing an example of the device for measuring optical properties for practicing the present invention. In FIG. 1, the device for measuring optical properties consists substantially of an exciting light source 3 for emitting excited light 2 to the site to be measured of a sample 1, an optical intensity modulator 4 for modulating the excited light 2, a probe light source 6 for emitting the probe light 5, an optical element 7 for leading the probe light 5 to the vicinity of the above site to be measured, a light position detector 8 for receiving the probe light 5, and an intensity distribution modifying means 9 for modifying the intensity distribution of the light flux of the probe light 5 so that the maximum intensity portion may contact approximately the sample 1 when the probe light 5 reaches the vicinity of the site to be measured. The exciting light 2 is focused by means of a separated optical element 7' to be irradiated on said site to be measured. On the other hand, the probe light 5 passes through the optical element 7, passing in parallel to the surface of the site to be measured of the sample 1 on which the above excited light 2 is irradiated, reaches the above light position detector 8, and the deflected amount X when deflected as shown by the dotted line 5' in the drawing is measured.

Figures 2A, 2B:
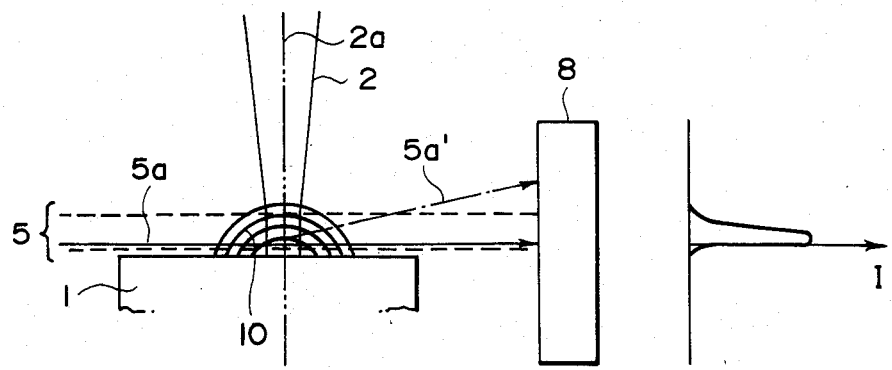
FIGS. 2A and 2B are schematic constitutional views for illustration of the basic principle in practicing the device for measuring optical properties and a light intensity distribution diagram, respectively.
Figures 3A, 3B:
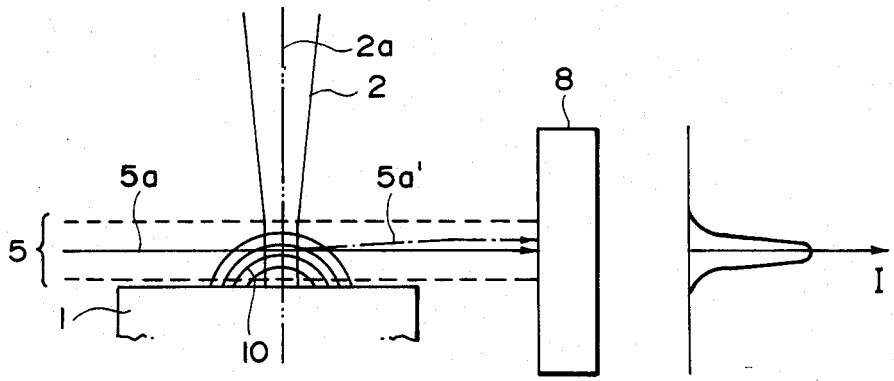
FIGS. 3A and 3B show a schematic constitutional illustration and a light intensity distribution diagram for a device for measuring optical properties of the prior art similar to FIGS. 2A and 2B.

FIGS. 2A and 2B are schematic constitutional views for illustration of the basic principle in practicing the device for measuring optical properties according to the present invention and a light intensity distribution diagram, respectively. In FIG. 2A, when an intermittent exciting light 2 is irradiated on the site to be measured of a sample 1 and the sample 1 absorbs light, intermittent heat is generated by the radiationless relaxation process, whereby the refractive index of light is intermittently fluctuated in the vicinity of the above site is to be measured. By passing a probe light 5 through the region where the refractive index fluctuation 10 is occurring and permitting deflection of the light flux center 5a to 5a' corresponding to the fluctuating refractive index to be incident on a light position detector 8, the fluctuation of the refractive index can be detected as the deflection of light. Here, the intensity distribution in the light flux of the probe light 5 can be measured on the plane along the exciting light axis 2a at the above site to be measured as shown in FIG. 2B. FIGS. 3A and 3B show schematic constitutional illustration and light intensity distribution diagram for a device for measuring optical properties of the prior art similar to FIG. 2. In the prior art, the intensity distribution is symmetric with respect to the light flux center 5a of the probe light, whereby it is impossible to make an approach to the sample nearer than the light flux width as shown by the dotted lines in the Figure and the deflection degree was small with the maximum intensity portion passing only through the edge of the fluctuated region. In contrast, in the present invention as shown in FIG. 2, the light flux shape of the probe light 5 is made asymmetric as shown in FIG. 2B and the probe light 5 is passed through the region with great refractive index fluctuation 10 so that the maximum intensity portion may be at the position nearest to the sample 1, whereby greater deflection 5a' as compared with FIG. 3 can be obtained.

Figure 4:
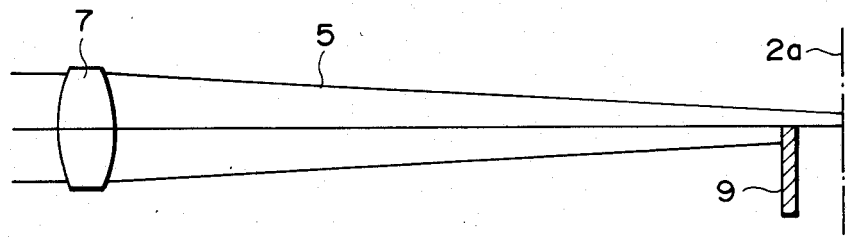
FIGS. 4 and 5 are schematic constitutional illustrations showing examples of the intensity distribution modifying means according to the present invention.

FIG. 4 is a schematic constitutional illustration showing an example of the intensity distribution modifying means according to the present invention for generating the above phenomenon. In FIG. 4, the intensity distribution modifying means is a light shielding plate 9 and it is arranged so as to cut half of the light flux at a position immediately before the probe light 5 is led to a lens 7 to reach the surface 2a of the site to be measured 2a. The probe light 5 of which the lower half in the drawing has been cut with this light shielding plate 9 is modified to a light flux with the maximum intensity being at the lower end in the drawing as shown in FIG. 2B, whereby it becomes possible to measure the region having the greatest refractive index fluctuation near the sample with maximum intensity portion of the light.

Figure 5:
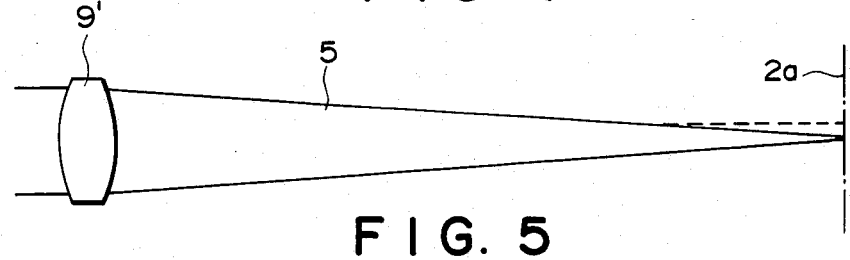

FIG. 5 is a schematic constitutional view showing another example of the intensity distribution modifying means according to the present invention, which is an example in which the optical element for focusing the probe light 5 has also the function of modifying intensity distribution. In FIG. 5, the polarizing lens 9' is previously designed so that the probe light 5 may be focused on the surface 2a of the site to be measured and at the same time the focused state may be at the maximum intensity around the sample side of light flux.

According to the present invention, a device for measuring optical properties with high sensitivity and high precision can be provided even for a sample with small light absorption such as a thin film being spread on a liquid surface, by permitting the greatest intensity portion of probe light to pass through the region with the greatest refractive index fluctuation caused by absorption.

Further, in the case of measuring optical properties by detecting the reflected light from a thin film which is the object to be measured by means of a position detector, since the sizes of light fluxes of exciting light and probe light as well as their relative positions will influence greatly the sensitivity, it is necessary to adjust these parameters.

For adjusting the sizes of the light fluxes of exciting light and probe light and their relative positions, there is the method in which strong scattered light is obtained by means of a scattering member and a method wherein an IR television camera is used for monitoring.

First, the method in which a scattering member is used is described.

As the scattering member to be used in the present invention, two kinds of members are mentioned: (1) a thin sheet and (2) a thin film giving strong scattered light spread internally of parts of a liquid surface divided with movable partitions.

According to the process of the present invention, since strong scattered light can be obtained, light fluxes of exciting light and probe light can be grasped clearly, whereby their sizes and relative positions can be easily adjusted and also measurement is possible under constantly the same conditions without causing change of the liquid surface when measuring a minute thin film which is the object to be measured. Also, since the region for spreading the scattering member is closed, the liquid surface for spreading the thin film which is the object to be measured will not be contaminated.

FIG. 6 through FIG. 9 show an example utilizing the present invention for measurement of light absorption characteristics of a monomolecular film spread on a liquid surface.

In FIG. 6A, 17 is a liquid tank containing a liquid 16 therein, and a thin film 13 giving strong scattered light is spread on the liquid surface 12 inside the partitions 14. From slightly below the liquid tank 17, a probe 5 is irradiated from the liquid 16 side toward the measuring site of the thin film 13. Further, an exciting light 2 is irradiated from the liquid 16 side toward the measuring site of the thin film 13. Also, when the partitions 14 are moved, on the clean water surface 11 outside of the partitions 14, the exciting light and the probe light are irradiated. On the water surface 11, a thin film which is the object to be measured is spread.

In the following, a specific measuring method is explained.

First, as shown in FIG. 6A, the probe light 5 and the exciting light 2 are irradiated toward the measuring site of the strongly scattering thin film 13 being spread on the liquid surface 12 inside the partitions 14, and, under observation of their scattered lights by the thin film 13 visually or with a television camera, the sizes of light fluxes of the probe light and the exciting light and their relative positions are adjusted. Next, as shown in FIG. 6B, with the conditions for the probe light 5 and the exciting light 2 being fixed, the partitions 14 are moved, whereby the probe light 5 and the exciting light 2 are irradiated on the clean liquid surface 11 outside of the partitions 14. By spreading a thin film 111 which is the object to be measured on the liquid surface 11, the light absorption characteristics of the thin film 111 can be instantly measured. In the Figure, 15 is a film-forming frame for applying a surface pressure on the thin film 111, when it is a monomolecular film.

Figure 7:
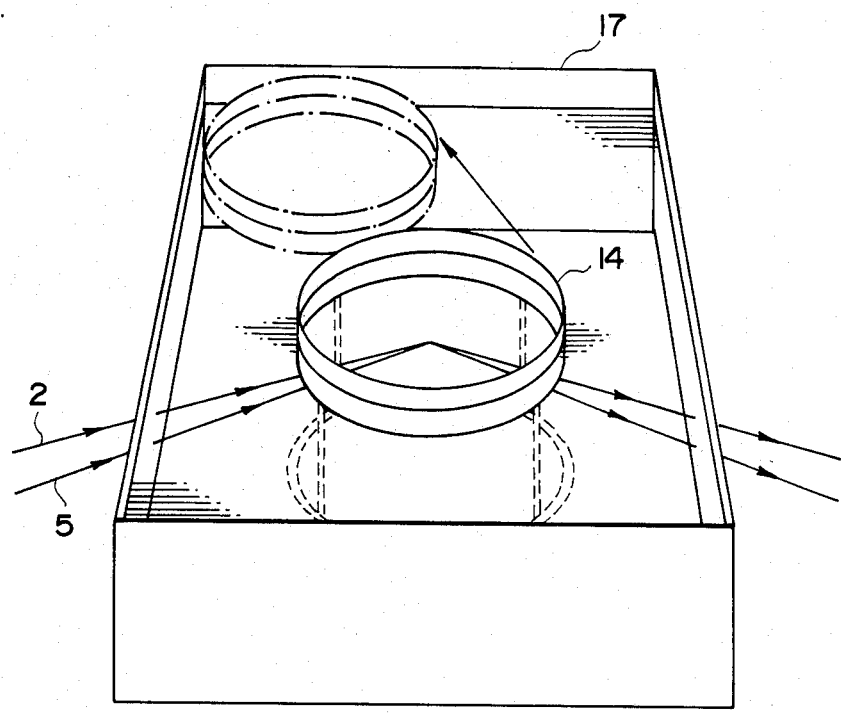
Figure 8:
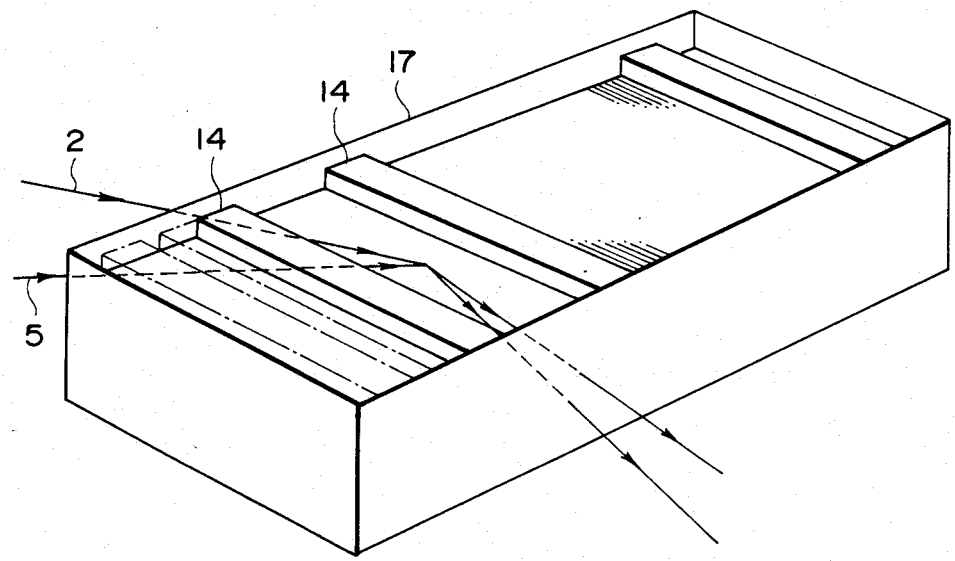

In the present invention, as the form of partitions 14, there is the method in which a closed region is formed as shown in FIG. 7 and the method in which a film-forming frame as shown in FIG. 8 is used. In either case, after adjustment of the light fluxes by a scattering member, the partitions 14 are moved to the position as indicated by dot-dash-lines so that the probe light 5 and the exciting light 2 may be irradiated on the clean liquid surface outside the partitions 14. In FIG. 7, the film-forming frame 15 for applying a surface pressure is omitted.

Figure 9:
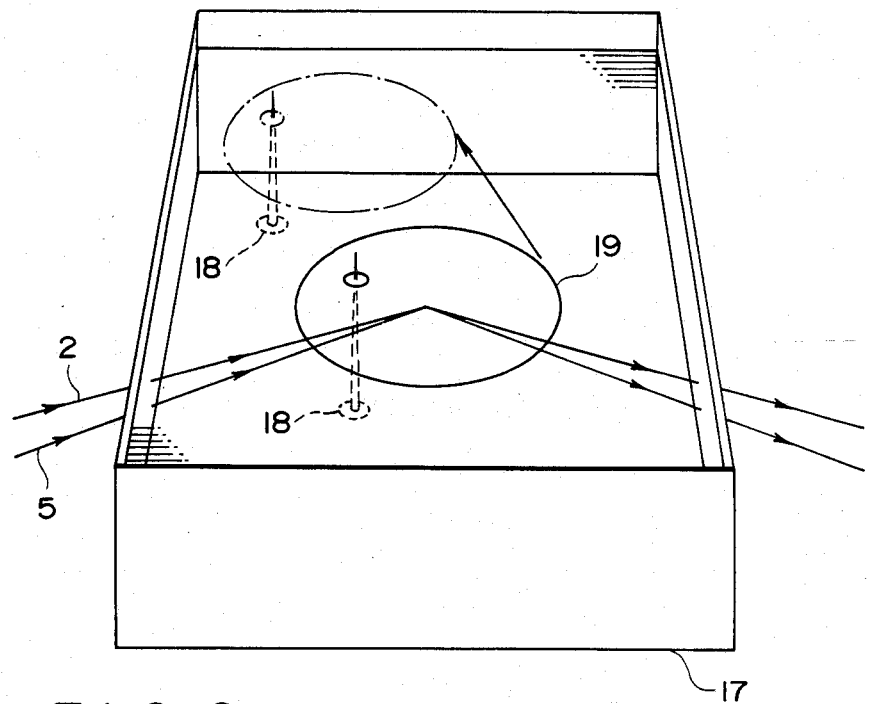

FIG. 9 shows a method of use of a scattering sheet in FIG. 9, a thin scattering sheet 19 is used in place of the partitions 14 and the thin film 13. The procedure in this case is the same as in the above example. In FIG. 9, the film-forming frame 15 for applying a surface pressure is omitted. And, 18 is a fixing pin for holding the scattering sheet 19 at the predetermined water surface.

As described above, according to the present invention, in the case of performing light absorption measurement for a film giving very weak scattered light such as a thin film spread on a liquid surface, particularly a monomolecular film, optical path adjustment, particularly adjustment of the light fluxes of probe light and exciting light as well as their relative positions can be done with extreme ease without changing the conditions around the thin film such as liquid surface, etc., whereby it is possible to carry out measurement with high precision and high sensitivity.

Figure 10:
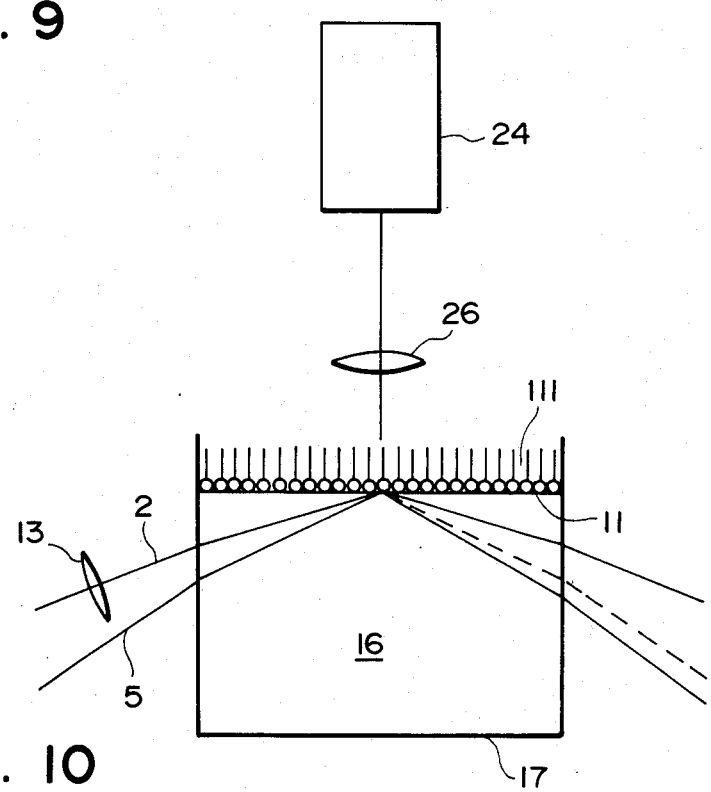
FIG. 10 illustrates use of an IR television camera for adjusting the positions of exciting light and probe light.

Another method for adjusting the positions where exciting light and probe light are irradiated and their relative position is the method in which an IR television camera is used. This is illustrated in FIG. 10. In the process according to the present invention, there is provided an IR television camera 24 for detecting the scattered light of exciting light 2 and probe light 5 at the thin film 111, and the sizes of the light fluxes of the excitation light 2 and the probe light 5 on the thin film 111 and their relative positions can be monitored. Accordingly, even in the case of a different film, measurement can be performed always under the same conditions. Further when wavelengths outside the visible region are used for the probe light 5 and the exciting light 2, by use of the IR television camera 24 having sensitivity to such wavelengths, the optical path can be easily adjusted to enable measurement with high precision.

In the following, the specific measuring method is explained.

The scattered light of the exciting light 2 and the probe light 5 at the thin film 111 on the liquid surface 11 are condensed by a lens 26 and received by the IR television camera 24, and the spots of the exciting light 2 and the probe light 5 on the liquid surface are shown on the screen. By monitoring the spots, it is possible to adjust the sizes of the light fluxes of the exciting light and the probe light as well as to adjust the relative positions of the spots of the exciting light and the probe light.

By monitoring thus the convergence state of the light flux of the exciting light and the probe light and the relative positional relationship of these, the fluctuation in optical path during measurement can be adjusted easily, and the physical properties of the thin film spread on the liquid surface can be precisely determined by measurement of the light absorption characteristic with high precision and high sensitivity, whereby the measuring working can be made simpler. Accordingly, by use of a monomolecular built-up film forming device, a monomolecular built-up film with very high characteristic precision can be obtained.

In the following, in the case of measuring, for example, a thin film spread on a liquid surface, means for preventing lowering in precision and sensitivity of measurement of light absorption characteristics due to fluctuation of liquid surface, etc. is explained.

FIGS. 11A and 11B show coordinate diagrams for illustration of the basic principle of the compensating method according to the present invention. In FIG. 11A, X-Y coordinate axes crossing at right angle with each other are set on the plane vertical to the average emitting direction of the light beam reflected from the sample surface, and the degree of deflection of the reflected light is shown by the arrow 112. If the above coordinate system is reversed by a suitable optical system, its projected image becomes X'-Y' as shown in FIG. 11B, and the deflection of the reflected light will also become as shown by the arrow 113. When the light beams reversed to each other are irradiated onto the target surface, their coordinates become point aymmetrical (112a, 113a) with respect to the original point 0 as shown in FIG. 11C. Also, the gravitational center of the light beam energy will constantly coincide with the original point 0, provided that both the light beam intensities are equal to each other. Accordingly, by use of an optical system satisfying the above conditions, the intensity center of the irradiated beam can be compensated without any influence even if fluctuation on the sample surface may occur by an external factor.

Figure 12:
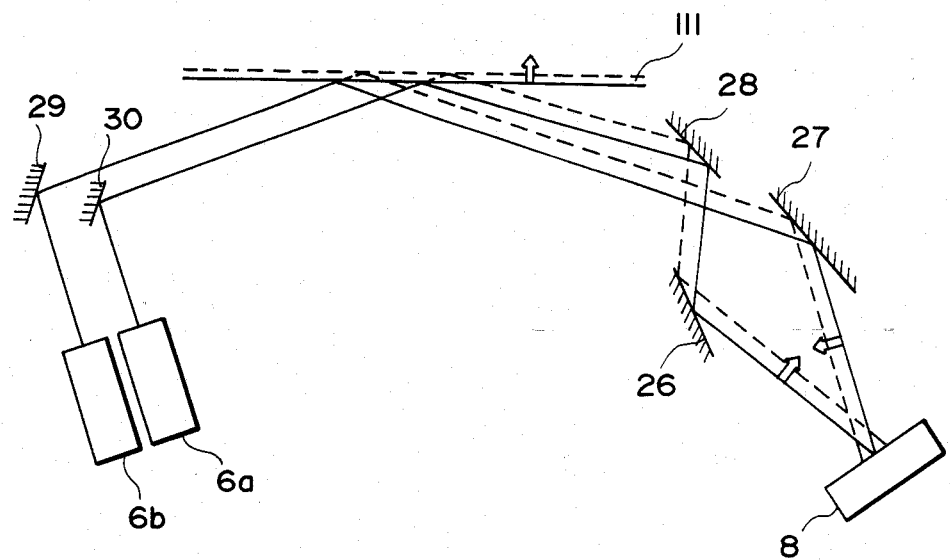
FIG. 12 is a schematic constitutional illustration of a basic device for verifying one-dimensionally the effect.
Figure 13A:
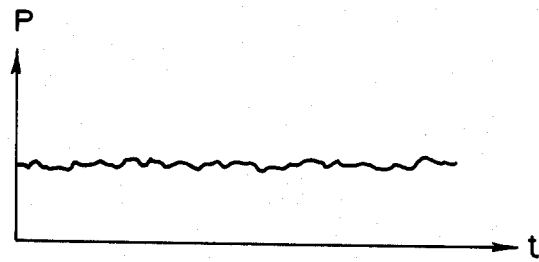
FIG. 13 is graphs illustrating the results of measurement of the positional deviation of the light beam according to the constitution of the present invention.
Figure 13B:
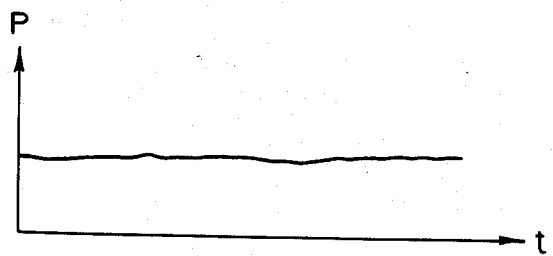

FIG. 12 is a schematic constitutional illustration of a basic device for verifying one-dimensionally the effect based on the above principle. The light beams from the two laser light sources 6a, 6b are irradiated on the sample surface 111 at the regions in close proximity to each other and the two pairs of separated light beams are irradiated by means of the mirrors 26, 27, 28 as the stabilizing optical systems onto a light position detector 8, respectively to record fluctuations on the sample surface 111. FIG. 13 shows graphs showing the results of measurement of the positional deviation of the light beam according to the above constitution, the axis of the ordinate indicating the detected position P of light beam and the axis of abscissa the time t. In FIG. 12, when only one light beam is irradiated directly onto the light position detector 8, the fluctuation on the sample surface 111 is recorded as shown in FIG. 13A, while the fluctuation on the sample surface is understood to be removed as shown in FIG. 13B when the compensation is effected according to the present invention.

This invention provides various stabilizing optical systems or other means based on the same principle which employ plural beams of the probe light to reduce measurement errors, thus giving measurement results independently of the fluctuation of the sample.

FIG. 14 is a constitutional illustration showing one example of a device for forming a monomolecular built-up film in which the present invention is practiced. In FIG. 14, 17 is liquid tank containing a liquid 16 therein and a thin film 111 which is the object to be measured is spread on the liquid surface 11. The thin film 111 shown in the Figure represents schematically a monomolecular film.

Slightly below the side of the liquid tank 17, probe light sources 6a and 6b are provided. From the probe light sources 6a and 6b, the probe lights 5a and 5b are irradiated from the liquid side 16 toward the measuring side of the thin film 111 at such angles that the light may be totally reflected against the liquid surface 11 on which the thin film 111 is spread. Also, at the opposed position to the probe light sources 6a and 6b with the liquid tank 17 interposed therebetween, there is provided a detector 8 for detecting the position of the probe light 5. The probe lights 5a and 5b are arranged so as to compensate for fluctuations by the external factors on the liquid surface 11 for each other on the light receiving surface of the above detector 8 based on the above principle by means of the mirrors 26, 27, 28 as the stabilizing optical systems. The signals from the detector 8 are sent through the driver 31 to the lock-in amplifier 32.

Above the liquid tank 17 is provided an exciting light source 3. The exciting light source 3 irradiate an exciting light 2 toward the measuring site of the thin film 111. At the position along the optical path of the exciting light 2, there is provided a light intensity modulator 4 such as a chopper or a variable filter, etc., for irradiating the exciting light 2 as an intermittent light or with accentuation of the light intensity. Also, the exciting light 2 is irradiated onto the measuring site of the thin film 111 by further being condensed through a lens 13.

The light intensity modulator 4 is connected to the lock-in amplifier 32, and the signal indicating the intermittent or accentuated state of the exciting light 2 sent from the light intensity modulator 7 can be used as the reference signal to detect synchronously the signal from the detector 8. The probe light sources 6a and 6b, the exciting light source 2, the light intensity modulator 4 and the rock-in amplifier 32 are respectively connected to a measurement controller 34. The measurement controller 34 controls optical paths and wavelengths of the probe lights 5a and 5b and the exciting light 2 as well as the intermittent or actuation interval of the exciting light 2 by means of the light intensity modulator 4, and also calculates light absorption characteristics by the signal from the lock-in amplifier 32.

The liquid tank 17 must not necessarily be entirely transparent, rather, so long as transparent windows are provided at least at the portions corresponding to the optical paths of the probe lights 5a and 5b and the exciting light 2. Also, the liquid 16 will have no considerable bad measurement effects even if more or less direct influence may be given, provided that it absorbs little of the exciting light 2, but it is preferred to be transparent.

First, the exciting light 2 emitted from the exciting light source 3 is modulated to an intermittent or accentuated light and irradiates the measuring site of the thin film spread on the liquid surface 11 in the liquid tank 17. In the region on the measuring site irradiated with the exciting light 2, the thin film 111 on the liquid surface 11 absorbs the light and generates heat intermittently or with actuation according to the radiationless radiation process, whereby refractive index change in the vicinity occurs intermittently.

On the other hand, the probe lights 5a and 5b emitted from the probe light sources 6a and 6b are permitted to enter at incident angles greater than the critical angles of the liquid 16 to be totally reflected at the site irradiated by the exciting light 2 of the liquid surface 11 and then pass through the liquid 16 out of the liquid tank 17. Accordingly, the probe lights 5a and 5b pass through the measuring site at which the refractive index changes intermittently by irradiation of the above exciting light 2. When the probe lights 5a and 5b emitted from the probe light sources 6a and 6b pass through the region where intermittent change of the refractive index occurs, the optical paths will be deflected corresponding to the refractive index distribution changed. When the beams of the probe light 5a and 5b are passed through the regions close to each other having different refraction index distributions, the mirrors 26, 27, and 28 as a stabilizing optical system serve to make zero the vector sum of the fluctuation of the probe light caused by the fluctuation of the liquid surface, thus the deflection of light depends only on the refractive index change cause by the exciting light irradiation.

The detector 8 receives continuously the probe lights 5a and 5b and sends the light-receiving positions of the probe lights 5a and 5b through the driver 31 to the lock-in amplifier 32. The lock-in amplifier 32 receives the signals from the detector 8 simultaneously with receiving the signals from the light intensity modulator 4 and, by synchronizing both signals, it can send the difference between the light-receiving position signal of the probe lights 5a and 5b on irradiation or at high intensity of the exciting light 2 and the light-receiving position signal of the probe lights 5a and 5b on nonirradiation or at low intensity of the exciting light 2 with good S/N ratio to the measurement controller 34. The measurement controller 34 determines the deflected amount of the probe lights 5a and 5b for the wavelength of the exciting light 2 at that time, and calculates the light absorption characteristics based thereon. Also, by performing similar measurements by varying successively the wavelength of the exciting light 2, the spectral absorption characteristics of the thin film 111 can be obtained.

In carrying out this measurement, the measuring site can be freely selected by controlling the optical path of the exciting light 2 by means of the measurement controller 34, and also the optical path of the probe lights 5a and 5b can be adjusted to achieve precision also by means of the measurement controller 34 corresponding to the position of the liquid surface 11. Further, it is possible to simplify the operation by performing automatically all of the controls necessary for the probe lights sources 6a and 6b, the exciting light source 3 and the light intensity modulator 4 by means of the measurement controller 34.

The light energy absorbed by the thin film 111 can be determined from the light quantity distribution at the measuring site of the exciting light 2, the characteristics of refractive index change of the liquid 16 by heat, the incident beam positions of the probe lights 5a and 5b and the degree of deflection at that time. Accordingly, if irradiation energy of the excited light 2 onto the thin film 111 is monitored by means of a photosensor, etc., absolute light absorption characteristics of the thin film 111 can be obtained from both energies. And, by varying the wavelength of the exciting light 2, absolute spectral absorption characteristics can be obtained. Also, only by determining previously the relative intensity at respective wavelengths of the exciting light 2 and determining the degree of deflection of the probe lights 5a and 5b corresponding to the wavelength, relative spectral absorption characteristics can be obtained. The relative values and absolute values of light absorption characteristics can be selected appropriately depending on the purpose of measurement.

Figure 35:
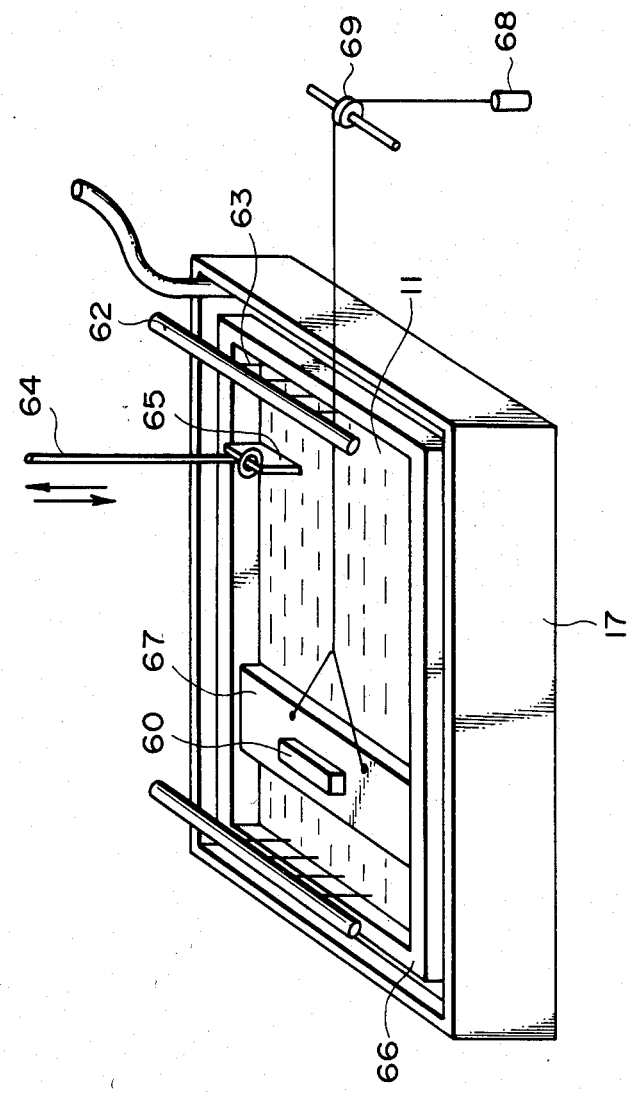
Figure 40:
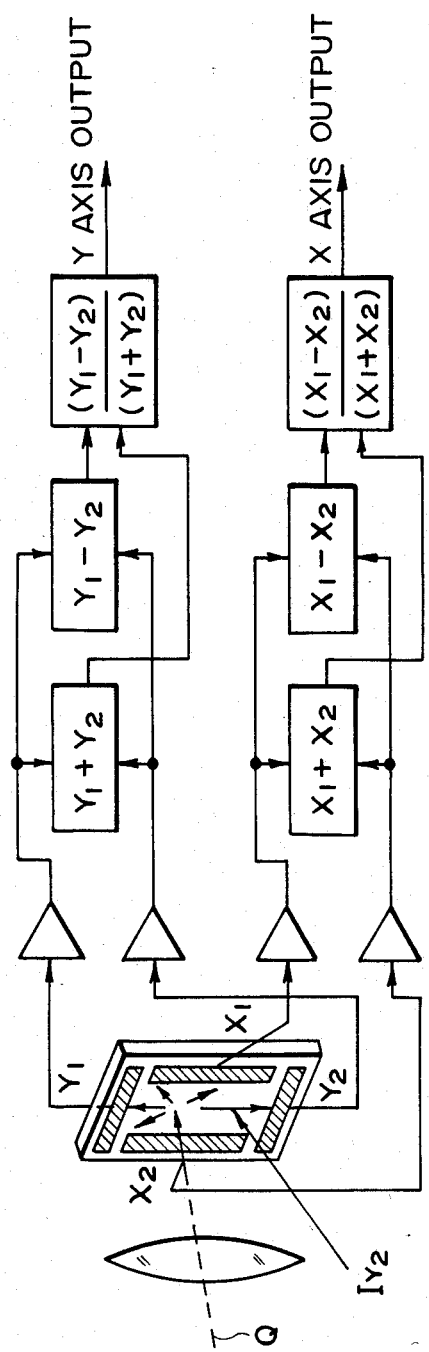
FIG. 40 is a block diagram of the actuation circuit of PSD.

Meanwhile, the constitution around the liquid tank 17 is similar to that of the device for forming monomolecular built-up film according to the LB method of the prior art, and this is explained by referring to FIG. 35 and FIG. 36.

The liquid tank 17 has an angular shape with a broad area and a shallow depth, having an inner frame 66 made of, for example, polypropylene, etc., suspended horizontally innerside thereof which partitions the liquid surface 11. As the liquid 16, pure water is generally employed. Inside the inner frame 66, there is floated a film forming frame 67 which is also made of, for example, polypropylene, etc. The film-forming frame 67 is in the form of a rectangular shape with its width being slightly shorter than the inner width of the inner frame 66, and is capable of two-dimensional piston movement in the right and left directions in the drawing. To the film-forming frame 67 is bound a weight 68 through a pulley 69 for drawing the frame toward the rightward direction in the Figure. Also, there is provided a magnet 60 fixed on the film-forming frame 67 and a counter-magnet 61 above the film-forming frame 67 capable of moving left and right in the drawing which will repel each other when the two magnet approach, whereby the film-forming frame 67 can be made move left and right in the drawings and also stopped. In place of such a weight 68 and a pair of magnets 60 and 61, a rotatary motor or a pulley can be used to move directly the film-forming frame 67.

On both sides within the inner frame 66, aspirating nozzles 63 connected through aspirating pipes 62 to aspirating pumps (not shown) are juxtaposed. These aspirating nozzles 63 are used for removing rapidly the monomolecular films, etc., of the preceding step which have become unnecessary on the liquid surface 11 for preventing mixing of monomolecular films or a build up of monomolecular films. 65 is a substrate which is mounted for vertical movement on a substrate holder 64.

The principles in forming a monomolecular film and obtaining a built-up film thereof by means of the device for forming monomolecular built-up film as described above is basically the same as those in the prior art.

First, the film forming-frame 67 is moved to clean the liquid surface 11 by sweeping and aspirating out the monomolecular films, etc., which have become unnecessary on the liquid surface 11 through aspirating nozzles 63. Next, with the film-forming frame 67 being moved to one end of the liquid tank 17, a film constituting material is added dropwise onto the liquid surface 11 and its spreading area is narrowed by movements of the film-forming frame 67 to form a solid film, followed by vertical movements of the substrate 65 thereby transferring the monomolecular film thereon.

Whereas, in the device according to this embodiment, as explained in FIG. 13, the physical properties of the thin film 111 which is the monomolecular film spread on the liquid surface 11 can be directly measured optically at the site where it is formed. Therefore, by controlling the movement of the counter-electrode 61 based on this measurement, namely the movement of the film-forming frame 67 by means of the measurement controller 64 through the steps from formation of the monomolecular film to its transfer, a monomolecular film with desired physical properties can be built up on the substrate 65.

FIG. 5 is a schematic constitutional view showing another embodiment of the present invention, in which a polarizer and a polarizing beam splitter are employed as the stabilizing optical systems, polarizers 33c and 33d are arranged ahead of the probe light sources 6c and 6d so as to polarize the two beams of the probe light 5c and 5d in the two directions perpendicular to each other (e.g. S polarization vertical to the paper plane and P polarization along the paper plane), both beams of light are irradiated on the measuring surface 111 by means of a polarizing beam splitter 31 under the state of both being substantially superposed on one another, reflected light is again split by a polarizing beam splitter 32 and the split light is superposed by means of the mirrors 26 and 27 on the light-receiving face of the detector 8 so as to compensate for fluctuations by the external factors on the liquid surface for each other. According to this constitution, the two light beams can be simply approximated to each other.

Figure 16:
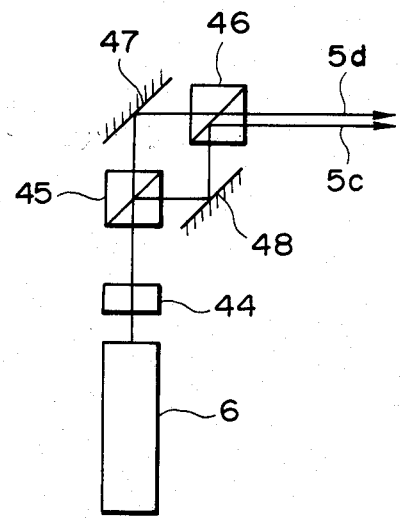

By use of a stabilizing optical system combining two polarizing splitters 45 and 46 with two mirrors 47 and 48 as shown in FIG. 16, it is possible to make two beams of the probe light 5c and 5d of the above S polarization and P polarization even by only one probe light source 6. That is, by arranging a polarizing plate 44 with λ/4 wavelength ahead of the probe light source 6 emitting directly polarizing light, separating as the circularly polarized light by means of the polarizing beam splitter 45 into S polarized light and P polarized light and, after reflection against the mirrors 47 or 48, superposing again by the polarizing beam splitter 46 on the same optical path, approximated S polarized light 5c and P polarized light 5d can be obtained.

Figure 19:
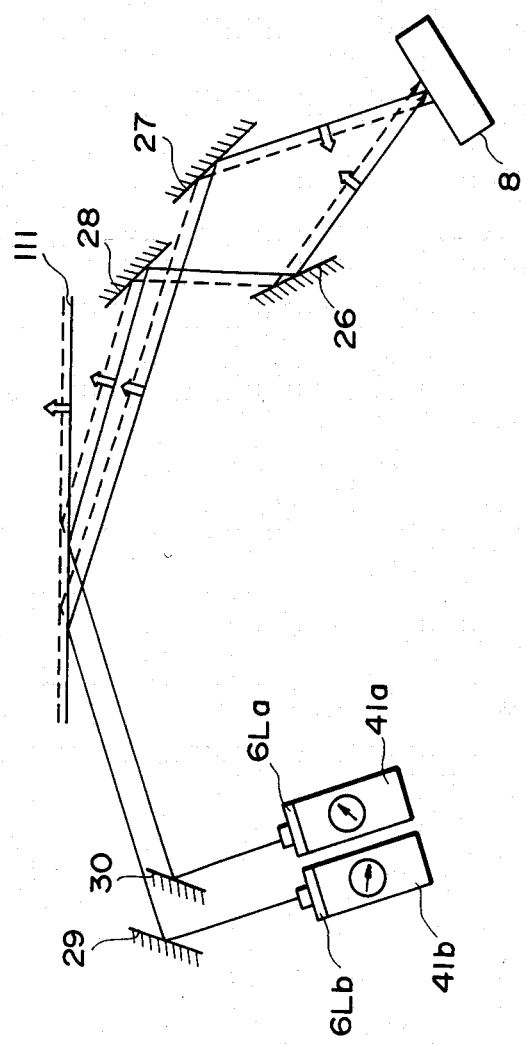

The respective Figures from FIG. 17 to FIG. 20 are schematic constitutional illustrations showing embodiments of the present invention provided with control means for making doses of the two probe lights equal on the light receiving surface of the detector. FIG. 17 and FIG. 18 show examples in which a variable ND filter is employed as the stabilizing optical system. In FIG. 17, variable NC filters 39a and 39b are arranged immediately ahead of the probe light sources 6c and 6d and, in FIG. 18, variable ND filters 40a and 40b are arranged immediately ahead of the detector 8. FIG. 19 shows an example in which semiconductor lasers 6La and 6Lb are used as the probe light source 6, and the light intensity of the probe light is controlled similarly as the stabilizing optical system by controlling the driving current of the laser by means of the drivers 41a and 41b.

Figure 20:
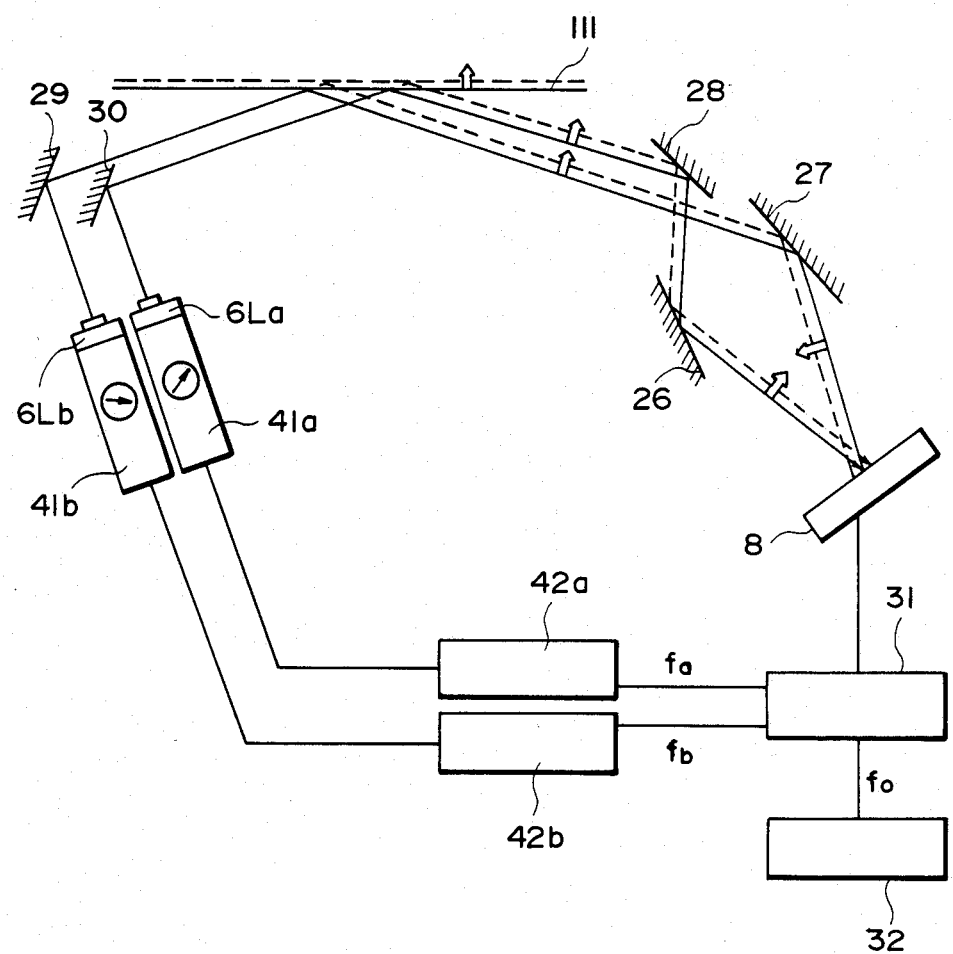

FIG. 20 shows an example for performing stable measurement by compensating the light intensity fluctuations of the two probe lights by using similarly semiconductor lasers 6La and 6Lb as the probe light sources. The probe light sources 6La and 6Lb are modulated with frequencies fa and fb different from the exciting light, the light intensity signals of the probe lights incident on the detector 10 are detected synchronously by means of the driver 31 with corresponding frequencies fa and fb, and feedback by the control drivers 42a and 42b is applied so as to compensate for light intensity fluctuations of the respective probe lights.

According to the present invention, the physical properties of a thin film spread on a liquid surface can be determined correctly by measurement of light absorption characteristics with high precision and high sensitivity and, when the device of the present invention is used for forming a monomolecular built-up film, monomolecular built-up films with extremely high precision characteristics can be obtained, whereby there can be provided a device for measuring optical properties of a thin film capable of giving stable measurement results by making zero the vector sum of the degree of deflection for each probe light caused by the fluctuations on the thin film surface such as wobbling of the liquid surface.

As another embodiment of the present invention, a device for measuring optical properties by irradiating an exciting light so as to be totally reflected against the liquid surface on a thin film spread on a liquid surface is explained. FIG. 21 is a schematic illustration of an embodiment of the present invention. On the side of a liquid tank 17, a probe light source 6 is provided. From the probe light source 6, probe light 5 is irradiated immediately beneath the liquid surface 11 and in the parallel direction to the liquid surface 11. Also, at the opposed position with the probe light source 6 and the liquid tank 11 interposed therebetween, there is provided a detector 8 for detecting the position of the probe light introduced. The signal from the detector 8 is transmitted through a driver 31 to a lock-in amplifier 32.

Slightly below the probe light source 6 is provided an exciting light source 3. The exciting light source 3 irradiates an exciting light 2 from the side of the liquid 16 toward the thin film 111 at such an incident angle that the light is totally reflected at the liquid surface 11 on which the thin film 111 is spreaded. At the position along the optical path of the exciting light 2 before entering the liquid tank 17, there is provided a light intensity modulator 4 for irradiating the exciting light 2 as the intermittent light.

First, the exciting light 2 emitted from the exciting light source 3 is modulated to an intermittent light by the light intensity modulator 4, then transmits through the window on the first mirror 53a on which said window is open and irradiates the measuring site of the thin film 111 spread on the liquid surface 11 in the liquid tank 17 from underneath. The exciting light 2 is thereby permitted to enter the liquid surface at an incident angle greater than the critical angle of the liquid 16, and after totally reflected by the liquid surface 11, comes out of the liquid tank 17 by passing through the liquid 16, reflected by the second mirror 53b and thereafter progresses in parallel to the liquid surface 11, and is again reflected by the mirror surface of the above first mirror 53a to irradiate the thin film 111. Similarly as before, the exciting light 2 totally reflected by the liquid surface 11 is reflected this time by the third mirror 53c which is in parallel to but slightly deviated in position from the second mirror, progresses in parallel to the liquid surface 11 and is then irradiated by another portion of the mirror surface of the first mirror 53a to irradiate the thin film 111. Thus, by repeating reflection in the order of the liquid surface 11→the second mirror 53b→the first mirror 53a→liquid surface 11→the third mirror 53c→the first mirror 53a, the exciting light 2 is irradiated in a plural number on the measuring site of the thin film 111. In the region of the respective measuring site against which the intermittent exciting light 2 is totally reflected, the thin film 111 on the liquid surface 11 absorbs light and generates heat intermittently according to radiationless relaxation process, whereby refractive index change in the vicinity will occur intermittently.

The light intensity modulator 4 is connected to a lock-in amplifier 32 and can detect synchronously the signal from the detector 8 with the signal indicating the intermittent state of the exciting light 2 transmitted from the light intensity modulator 4 as the reference signal. The probe light source 6, the exciting light source 3, the light intensity modulator 4 and the lock-in amplifier 32 are each connected to a measurement controller 34. The measurement modulator 34 controls the optical paths and wavelengths of the probe light 5 and the exciting light 2 as well as the intermittent intervals of the exciting light 2 by means of the light intensity modulator 4, and also calculates the light absorption characteristics by the signal from the lock-in amplifier 32.

The liquid tank 17 must not necessarily be completely transparent, rather transparent windows must be provided on at least the portions which become the optical paths of the probe light 5 and the exciting light 2. The liquid 16 will not give bad measurement reflects even if more or less direct influence may be given on the probe light 5, provided that it absorbs little of the exciting light 2. But, all in all, it is preferred to be transparent.

On the other hand, the probe light 5 emitted from the probe light source 6 passes immediately below the liquid surface 11 in parallel thereto, thus passing through the vicinity of the measuring site at which refractive index changes intermittently by radiation of the above exciting light 2. When the probe light 5 emitted from the probe light source 6 passes through the region where such an intermittent change of refractive index occurs, the optical path will be deflected as shown by the broken line corresponding to the change refractive index distribution.

The detector 8 receives continuously the probe light 5 and sends the light-receiving position of the probe light 5 through the driver 31 to the lock-in amplifier 32. The lock-in amplifier 32 receives the signal from the detector 8 simultaneously with receiving the signal from the light intensity modulator 4 and, by synchronizing both signals, sends the light-receiving position signal of the probe light 5 during radiation of the exciting light 2 and the light-receiving position signal of the probe light 5 on non-irradiation of exciting light 2 as separated with good S/N ratio to the measurement controller 34. The measurement controller 34 determines the degree of deflection of the probe light 5 for the wavelength of the exciting light at that time based on the signals sent and thus calculates light absorption characteristics based thereupon. Also, by carrying out similar measurements by varying successively the wavelength of the exciting light 2, spectral absorption characteristics of the thin film 111 can be obtained.

In carrying out the measurement, the measuring site can be selected freely by controlling the optical path of the exciting light 2 by means of the measurement controller 34, and measurement can be made more precise by controlling the optical path of the probe light 5 also by the measurement controller depending on the position of the liquid surface 11. It is also possible to simplify the operation of performing all of the controls necessary for the probe light source 6, the exciting light source 3 and the light intensity modulator 4 automatically by means of the measurement controller 34.

The light energy absorbed by the thin film 111 is determined from the light quantity distribution of the exciting light 2 at the measuring site, the characteristics of refractive index change of the liquid 16 by heat, the incident beam position of the probe light 5 and the degree of reflection at that time. Accordingly, if the irradiation energy of the exciting light 2 onto the thin film 111 is monitored by a photosensor, etc., absolute light absorption characteristics of the thin film 111 can be obtained from both energies. And, by varying the wavelength of the exciting light 2, absolute spectral absorption characteristics can be obtained. Further, only by previously determining the relative intensities of the exciting light 2 at respective wavelengths and determining the deflected amounts of the probe lights 5 corresponding to the wavelengths, can relative spectral absorption characteristics be obtained. The relative values or absolute values of light absorption characteristics may be selected suitably depending on the purpose of measurement.

Figure 22:
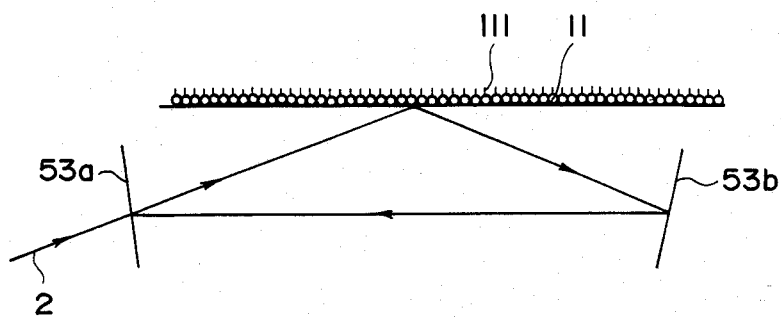
FIGS. 22 and 23 illustrate the basic principle of the present invention.
Figure 23:
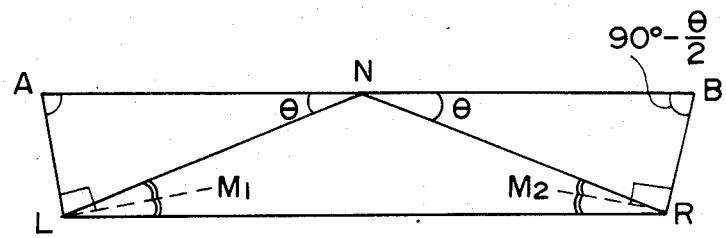

FIG. 22 and FIG. 23 illustrate the basic principle of the present invention. In FIG. 22, a thin film 111 as the sample is spread on the liquid surface 11, and the exciting light 2 is permitted to enter from below the liquid surface 11 at such an angle that the liquid is totally reflected by the liquid surface and, after totally reflected, it is reflected by a mirror 53b in the direction parallel to the liquid surface 11, and reflected again by a mirror 53a to irradiate the thin film 111 on the liquid surface 11. Now, the total reflecting position on the liquid surface is defined as N, the reflection position on the mirror 13b as R, the crossing position between the mirror surface and the liquid surface as B, the reflection position on the mirror 53a as L and the crossing position between the mirror surface and the liquid surface as A. Then, when the incident angle <LNA is $\theta$, the total reflection angle <RNB also becomes $\theta$, and, if the mounting angle of the mirror is set so that the reflected light RL may be parallel to the liquid surface AB, the angle formed between the normal line $M_2$ at the reflection position R and the exciting light NR becomes $\theta/2$, and the angle <RBN formed between the mirror 53b and the liquid surface AB becomes $90 - \theta/2$. On the other hand, for the exciting light RL in parallel with the liquid surface to be reflected again at the point L in the direction toward the point N, the angle formed between the normal line $M_1$ and the exciting light RL may be set to be $\theta/2$, and in that case the angle <LAN formed between the mirror 53a and the liquid surface AB becomes $90 - \theta/2$.

However, in FIG. 23, in the mirror 53a, the transmission position of the exciting light overlaps the re-reflection position L of the reflection from the liquid surface, and therefore it is impossible to increase both transmission and reflection, whereby the overall exciting light intensity cannot be increased. Accordingly, with the mounting angle of the mirror 53b being maintained as such, the mounting position can be slightly shifted to change the height of the exciting light in parallel to the liquid surface, whereby transmission and reflection will not overlap each other as in the embodiment shown in FIG. 21.

Figure 24:
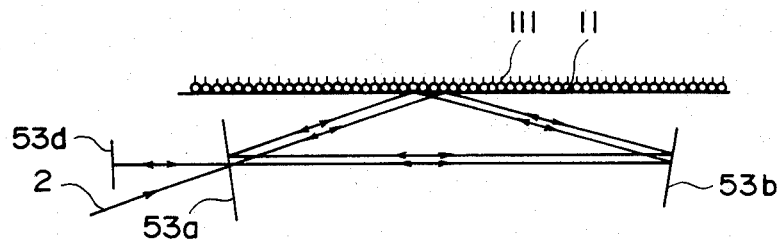
FIGS. 24 through 34 illustrate embodiments of the present invention.

FIG. 24 illustrates another embodiment of the present invention, in which only the portion where the exciting light 2 is irradiated onto the thin film 111 on the liquid surface is shown. The exciting light 2 passes through the opening window at the mirror 53a at such an angle that the light is totally reflected by the liquid surface 11, and then reflected against the mirror 53b so as to irradiate the mirror 53a at a position in parallel with the liquid surface 11 and shifted from the above opening window. The exciting light is again reflected by the mirror 53a, enters the liquid surface 11 at the same incident angle as in the previous time, is reflected again by the mirror 53b in the direction parallel with the liquid surface 11 and then transmits through the above opening window. When the transmitted light is reflected vertically by the mirror 53d, the exciting light 2 returns in the opposite direction of the same optical path, whereby the thin film 111 on the liquid surface is irradiated a total of four times.

Figure 25:
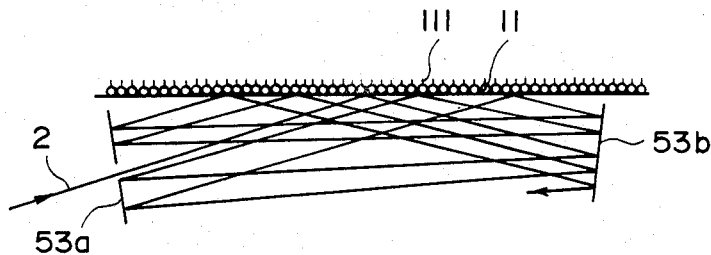
Figure 26:
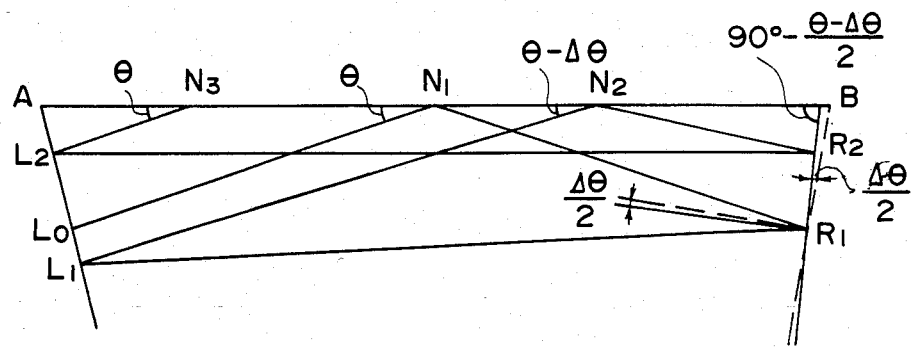

FIG. 25 and FIG. 26 illustrate still another embodiment of the present invention, FIG. 25 showing the constitution of the portion where the exciting light 2 is irradiated onto the thin film 111 on the liquid surface 11, and FIG. 26 showing the principle of how the exciting light 2 totally reflected by the liquid surface 11 is irradiated repeatedly onto the thin film 111 on the liquid surface 11. This embodiment has the second mirror 53b as shown in FIG. 22 and FIG. 23 mounted at an angle shifted by a minute angle ($\Delta\theta/2$ in the normal direction) from that in FIG. 22 and FIG. 23, whereby the position at which the reflected light is introduced on the first mirror 53a is shifted correspondingly. With such a constitution, as shown in FIG. 26, by making the angle $\theta$ formed between the liquid surface 11 and the exciting light 2 at the first exciting light irradiation position $N_1$, the incident angle for the second exciting light irradiation position $N_2$ becomes $\theta - \Delta\theta$, and then the angle becomes $\theta$ for the third time, whereby the thin film 111 on the liquid surface can be irradiated repeatedly.

Figure 27:
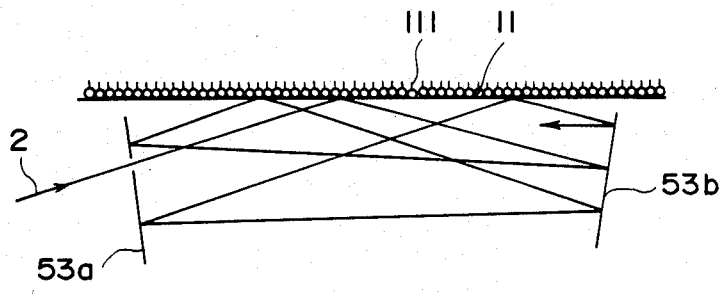
Figure 28:
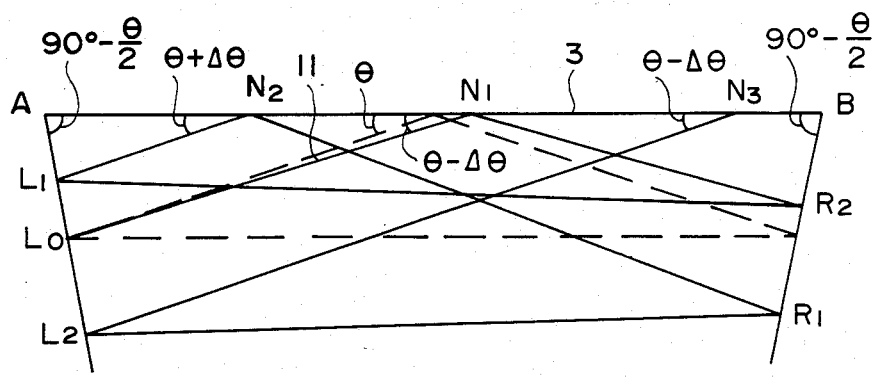
Figure 29:
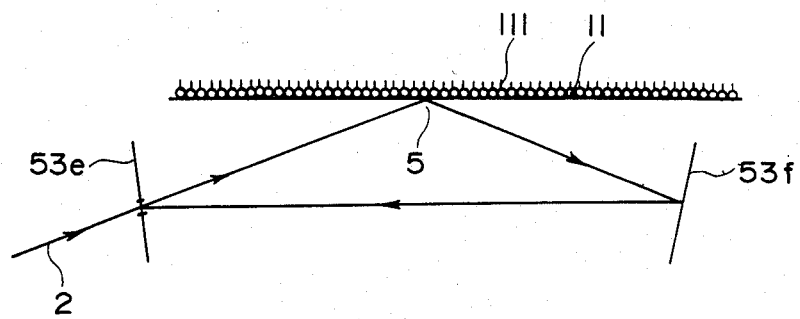

FIG. 27 and FIG. 28 illustrate still another embodiment of the present invention, FIG. 27 showing the constitution of the portion where the exciting light 2 is irradiated onto the thin film on the liquid surface 11, and FIG. 29 showing the principle how the exciting light 2 totally reflected against the liquid surface 11 is irradiated repeatedly onto the thin film 111 on the liquid surface 11. This embodiment has the same mirror arrangement as shown in FIG. 22 and FIG. 23 except that the angle at which the exciting light 2 is incident on the above thin film 111 is shifted by $\Delta\theta$ from $\theta$ to $\theta - \Delta\theta$. With such a constitution, as shown in FIG. 28, when the angle formed between the liquid surface 11 and the exciting light 2 at the first exciting light irradiation position $N_1$ is $\theta - \Delta\theta$, the incident angle at the second exciting light irradiation position $N_2$ becomes $\theta + \Delta\theta$, then again $\theta - \Delta\theta$ for the third time, repeating subsequently $\theta - \Delta\theta$ and $\theta + \Delta\theta$ every other time, thus enabling repeated irradiation onto the thin film 111 on the liquid surface 11.

Figure 30:
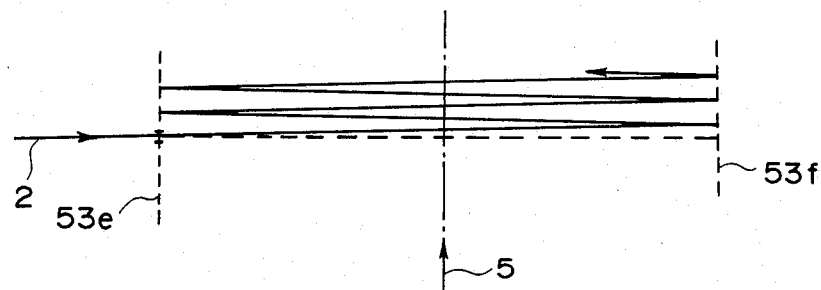

FIG. 29 and FIG. 30 illustrate still another embodiment of the present invention, with FIG. 29 showing a sectional view of the constitution of the portion where the exciting light 2 is irradiated onto the thin film 111 on the liquid surface 11, and FIG. 30 showing a lateral sectional view of the positional relationship between the exciting light 2 and the probe light 5. This embodiment has the same mirror arrangement as shown in FIG. 22 and FIG. 23 except that an optical system is used so as to give a deviation to the incident angle of the exciting light 2 as shown in FIG. 30. Accordingly, the exciting light 2, which appears to pass along the same optical path in the same irradiation device in the longitudinal sectional view, is reflected repeatedly on the actual liquid surface 11 by moving, in small increments the irradiated position of the thin film 111. By permitting the probe light 5 to pass as shown by the broken line in FIG. 30 immediately below the tentative line connecting serially the moved irradiation positions, a large deflected amount can be obtained.

Figure 31:
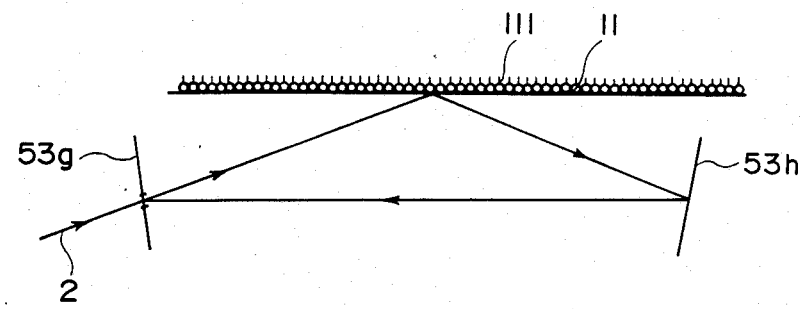
Figure 32:
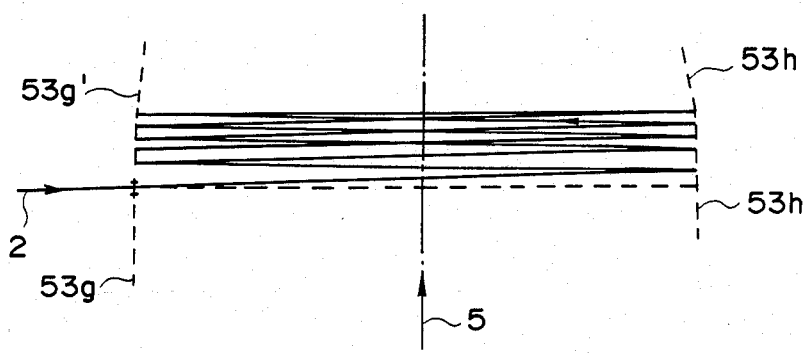

FIG. 31 and FIG. 32 illustrate still another embodiment of the present invention, with FIG. 31 showing a sectional view of the constitution of the portion where the exciting light 2 is irradiated onto the thin film 111 on the liquid surface 11, and FIG. 32 showing a lateral sectional view of the positional relationship between the exciting light 2 and the probe light 5. In this embodiment, one portion of a pair of the mirrors 53e and 53h as shown in FIG. 29 and FIG. 30 are constituted of a pair of mirrors 53g and 53h bent or warped toward the opposed sides. Accordingly, the irradiation position of the exciting light 2 relative to the thin film 111 on the liquid surface 11 will be initially shifted little by little in one direction similarly as in the case of FIG. 30, but on reaching the above bent portions 53g' and 53h', the angle of reflection changes, whereby the exciting light irradiation position on the thin film 111 moves conversely to be returned again to the initial position. As a result, the region of the exciting light irradiation position can be restricted to a local area which is not too broad. The above bending or warping can be provided on both sides of the incident points of the mirrors 53g and 53h, and further localization is also possible.

Figure 33:
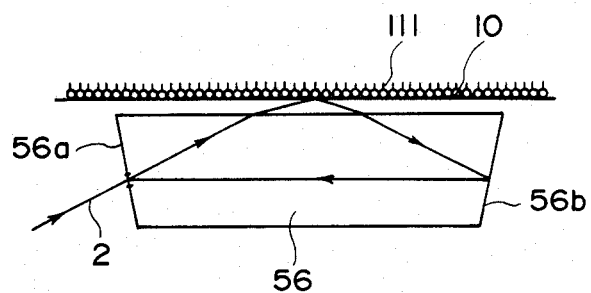
Figure 34:
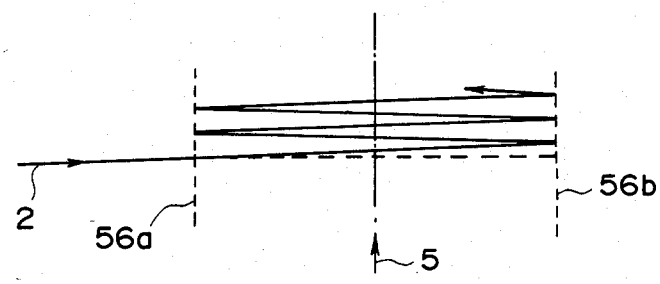

FIG. 33 and FIG. 34 illustrate still another embodiment of the present invention, with FIG. 33 showing a sectional view of the constitution of the portion where the exciting light 2 is irradiated onto the thin film 111 on the liquid surface 11, and FIG. 34 showing a lateral sectional view of the positional relationship between the exciting light 2 and the probe light 5. This embodiment substitutes two faces 56a and 56b of a prism 56 for a pair of mirrors 53e and 53f in the constitution as shown in FIG. 29 and FIG. 30, thereby permitting the exciting light 2 to pass through the prism 56.

This enables easy adjustment by integrating the optical system by forming the side faces of the prism for the reflecting surfaces in place of the mirror surfaces. This system of employing prisms in place of mirrors is not limited to this embodiment, but applicable to each of other embodiments of the present invention as already described above, as a matter of course.

Measurement of optical properties according to the present invention is beneficial when utilized in obtaining monomolecular built-up films by use of a liquid tank as shown in FIG. 35 and FIG. 36. According to the present invention, in carrying out measurement of light absorption characteristics of a thin film spread on a liquid surface, influences from reflected light and transmitted light as well as deleterious influences on the exciting beam from dust or fluctuation in the air can be excluded to enable measurement with high sensitivity and high precision.

Further, the exciting light can be reflected against the liquid surface and the mirror surface for a number of times and irradiated for plural times onto the measuring site to increase the overall exciting intensity and the probe light deflection region, whereby high sensitivity detection becomes possible with an enlarged deflection angle of the probe light.

We claim:

1. A device for measuring optical properties, comprising:
   an exciting light source for emitting exciting light to a site of a sample to be measured;
   a light intensity modulator for modulating the exciting light;
   a probe light source for emitting a probe light having an intensity distribution;
   a light position detector for receiving the probe light; and
   intensity distribution modifying means for bringing a gravitational center of the light intensity distribution of said probe light close to the sample when the probe light emitted from the probe light source approaches the site to be measured.

2. A method for measuring optical properties, comprising the steps of:
   irradiating an exciting light to a site of a sample to be measured;
   irradiating a probe light having a flux on the site to be measured or in a vicinity thereof such that the probe light enters a light position detector; and
   measuring the optical properties of the sample from the degree of deflection of the probe light by forming the flux of the probe light with an intensity distribution such that a gravitational center of light intensity distribution at the site of the sample to be measured is close to the sample.

3. A device for measuring optical properties, comprising:
   a liquid tank for containing a liquid;
   means for spreading a thin film on a surface of the liquid;
   an exciting light source for emitting exciting light to be irradiated on a site of the thin film to be measured;
   an optical intensity modulator for modulating intensity of the exciting light before reaching said measuring site;
   a probe light source for emitting probe light to be irradiated on the measuring site at an incident angle so as to be totally reflected at the liquid surface;
   a light position detector for detecting the degree of deflection of the probe light passed through said measuring site; and
   intensity distribution modifying means for bringing a gravitational center of light intensity distribution of the probe light close to the sample when the probe light omitted from said probe light source approaches the site to be measured.

4. A method for measuring optical properties, comprising the steps of:
   irradiating excited light onto a site of a sample to be measured
   irradiating probe light on the site to be measured or in the vicinity thereof such that the probe light enters a light position detector, wherein the probe light comprises at least two beams;
   measuring the optical properties of the sample from the degree of deflection of the probe light;
   setting an optical system so as to make the vector sum of fluctuation of the respective beams from a standard point on a detecting surface caused by fluctuation of the sample invariably zero; and
   modifying an intensity distribution of the probe light so as to bring the gravitational center of the probe light to the site of the sample to be measured.

5. A device for measuring optical properties, comprising;
   a liquid tank for containing a liquid
   means for spreading a thin film on a surface of the liquid;
   an exciting light source for emitting exciting light to irradiate a site of the thin film to be measured at an incident angle so as to be totally reflected at the liquid surface;
   optical means for permitting the exciting light totally reflected at the liquid surface to be incident again onto the site to be measured at an angle so as to be totally reflected at the liquid surface;

an optical intensity modulator for modulating the intensity of the exciting light before reaching the site to be measured;

a probe light source for emitting probe light to pass through the site to be measured or in the vicinity thereof;

a light position detector for detecting the degree of the deflection of the probe light passed through the site to be measured or in the vicinity thereof; and an intensity distribution modifying means for bringing a gravitational center of light intensity distribution of said probe light close to the sample when the probe light emitted from the probe light source reaches the site to be measured.

6. A device according to claim 1, wherein said intensity distribution modifying means comprises a light shielding plate.

7. A device according to claim 1, wherein said intensity distribution modifying means comprises a polarizer.

8. A device according to claim 1, further comprising:
means for adjusting a position of projection of the exciting light and the probe light.

9. A device according to claim 8, wherein said means for adjusting the position of projection comprises a light scattering means.

10. A device according to claim 8, wherein said means for adjusting the position of projection comprises an infrared television camera.

* * * * *

UNITED STATES PATENT AND TRADEMARK OFFICE
CERTIFICATE OF CORRECTION

PATENT NO. : 4,790,664

DATED : December 13, 1988

INVENTOR(S) : Kenji Saito et al.

It is certified that error appears in the above-identified patent and that said Letters Patent is hereby corrected as shown below:

AT [56] IN THE REFERENCES CITED

Line 3, change "4,299,494 11/1987 Badoz, et al:" to --4,299,494 11/1981 Badoz, et al.

COLUMN 3

Line 35, change "monomelecular" to --monomolecular--.

COLUMN 5

Line 50, delete "and"; and

Line 54, after "Therefore" insert --,-- (comma).

COLUMN 6

Line 66, delete "irradiate".

COLUMN 7

Line 60, change "present invention" to --according to the present invention--; and Line 63, before "graphs" delete "is and insert -- are --.

UNITED STATES PATENT AND TRADEMARK OFFICE
CERTIFICATE OF CORRECTION

PATENT NO. : 4,790,664

DATED : December 13, 1988

INVENTOR(S) : Kenji Saito et al.

It is certified that error appears in the above-identified patent and that said Letters Patent is hereby corrected as shown below:

COLUMN 9

Line 27, before "light" insert --a--.

COLUMN 12

Line 28, change "aymmetrical" to --asymmetrical--.

COLUMN 14

Line 16, change "cause" to --caused--.

COLUMN 15

Line 27, before "move" insert --to--.

COLUMN 16

Figure 15:
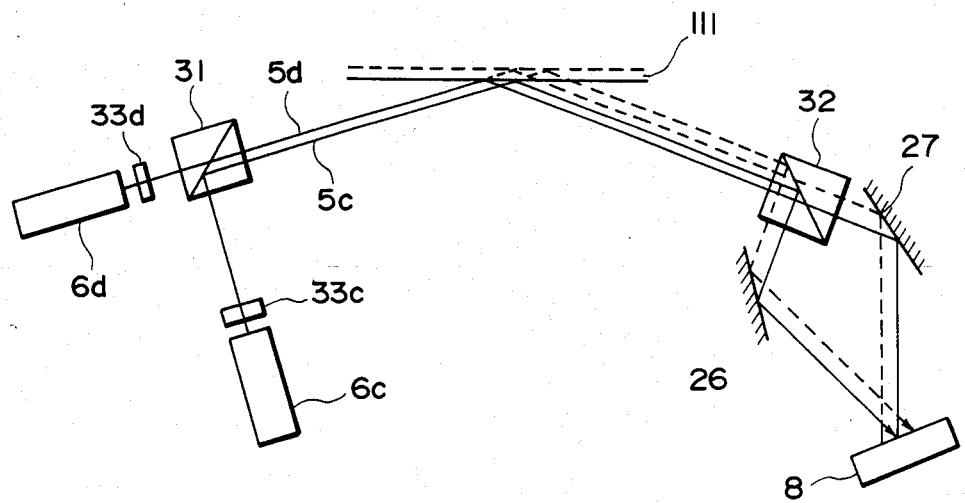
FIGS. 15 and 16 are a schematic constitutional view showing another embodiment of the present invention in which a polarizer and a polarizing beam splitter are provided as the stabilizing optical systems.

Line 1, change "FIG. 5" to --FIG. 15--.

UNITED STATES PATENT AND TRADEMARK OFFICE
CERTIFICATE OF CORRECTION

PATENT NO. : 4,790,664

DATED : December 13, 1988

INVENTOR(S) : Kenji Saito et al.

It is certified that error appears in the above-identified patent and that said Letters Patent is hereby corrected as shown below:

COLUMN 18

Line 29, before "refractive" insert --in--.

COLUMN 19

Line 68, delete "then".

COLUMN 20

Line 18, before "is" insert --and--.

COLUMN 22

Line 39, change "omitted" to --emitted--;

Line 44, after "measured" insert --;-- (semicolon); and

Line 60, after "liquid" insert --;-- (semicolon).

Signed and Sealed this

Thirteenth Day of February, 1990

*Attest:*

JEFFREY M. SAMUELS

*Attesting Officer*　　　*Acting Commissioner of Patents and Trademarks*